(12) United States Patent
Klassen et al.

(10) Patent No.: US 10,403,170 B2
(45) Date of Patent: *Sep. 3, 2019

(54) METHODS OF TREATING OVERWEIGHT AND OBESITY

(71) Applicant: Nalpropion Pharmaceuticals, Inc., Morristown, NJ (US)

(72) Inventors: Preston Klassen, La Jolla, CA (US); Kristin Taylor, San Diego, CA (US)

(73) Assignee: Nalpropion Pharmaceuticals, Inc., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/491,870

(22) Filed: Apr. 19, 2017

(65) Prior Publication Data

US 2017/0221380 A1 Aug. 3, 2017

Related U.S. Application Data

(63) Continuation of application No. 14/405,775, filed as application No. PCT/US2013/044368 on Jun. 5, 2013, now Pat. No. 9,633,575.

(60) Provisional application No. 61/656,451, filed on Jun. 6, 2012.

(51) Int. Cl.
| | |
|---|---|
| G09B 5/06 | (2006.01) |
| G06F 19/00 | (2018.01) |
| G09B 19/00 | (2006.01) |
| A61K 31/137 | (2006.01) |
| A61K 31/485 | (2006.01) |
| G01G 19/414 | (2006.01) |

(52) U.S. Cl.
CPC ........ *G09B 19/0092* (2013.01); *A61K 31/137* (2013.01); *A61K 31/485* (2013.01); *G01G 19/4146* (2013.01); *G06F 19/3456* (2013.01); *G09B 5/065* (2013.01)

(58) Field of Classification Search
CPC .................................................. A61K 31/485
USPC .............................................. 514/282, 909
See application file for complete search history.

(56) References Cited

U.S. PATENT DOCUMENTS

| | | |
|---|---|---|
| 3,819,706 A | 6/1974 | Mehta |
| 3,885,046 A | 5/1975 | Mehta |
| 3,942,641 A | 3/1976 | Segre |
| 4,089,855 A | 5/1978 | Chatterjie et al. |
| 4,172,896 A | 10/1979 | Uno et al. |
| 4,218,433 A | 8/1980 | Kooichi et al. |
| 4,295,567 A | 10/1981 | Knudsen |
| 4,451,465 A | 5/1984 | White et al. |
| 4,483,846 A | 11/1984 | Koide et al. |
| 4,513,006 A | 4/1985 | Maryanoff et al. |
| 4,673,679 A | 6/1987 | Aungst et al. |
| 4,689,332 A | 8/1987 | McLaughlin et al. |
| 4,828,836 A | 5/1989 | Elger et al. |
| 4,831,031 A | 5/1989 | Lowe et al. |
| 4,855,306 A | 8/1989 | Markstein et al. |
| 4,895,845 A | 1/1990 | Seed |
| 5,000,886 A | 3/1991 | Lawter et al. |
| 5,028,612 A | 7/1991 | Glover |
| 5,082,864 A | 1/1992 | Van den Oetelaar et al. |
| 5,202,128 A | 4/1993 | Morella et al. |
| 5,213,807 A | 5/1993 | Chemburkar et al. |
| 5,213,808 A | 5/1993 | Bar-Shalom et al. |
| 5,283,263 A | 2/1994 | Norden |
| 5,312,925 A | 5/1994 | Allen et al. |
| 5,358,970 A | 10/1994 | Ruff et al. |
| 5,364,841 A | 11/1994 | Cooper et al. |
| 5,403,595 A | 4/1995 | Kitchell et al. |
| 5,426,112 A | 6/1995 | Zagon et al. |
| 5,427,798 A | 6/1995 | Ludwig et al. |
| 5,486,362 A | 1/1996 | Kitchell et al. |
| 5,512,593 A | 4/1996 | Dante |
| 5,541,231 A | 7/1996 | Ruff et al. |
| 5,626,874 A | 5/1997 | Conte et al. |
| 5,714,519 A | 2/1998 | Cincotta et al. |
| 5,716,976 A | 2/1998 | Bernstein |
| 5,719,197 A | 2/1998 | Kanios et al. |
| 5,731,000 A | 3/1998 | Ruff et al. |
| 5,738,874 A | 4/1998 | Conte et al. |
| 5,763,493 A | 6/1998 | Ruff et al. |
| 5,817,665 A | 10/1998 | Dante |
| 5,817,666 A | 10/1998 | Katz |

(Continued)

FOREIGN PATENT DOCUMENTS

| | | |
|---|---|---|
| CA | 2317044 | 7/1999 |
| EP | 0 005 636 | 11/1979 |

(Continued)

OTHER PUBLICATIONS

A multicenter, randomized, double-blind, placebo-controlled study assessing the occurrence of major adverse cardiovascular events (MACE) in overweight and obese subjects with cardiovascular risk factors receiving naltrexone SR/bupropion SR, Adis Clinical Trials Insight (Nov. 15, 2011), 5 pp.
Ackerman et al., 1998, Clinical characteristics of response to fluoxetine treatment of obsessive-compulsive disorder. Journal of Clinical Psychopharmacology, 18(3):185-192.
Adis Data Information BV, 2010, Naltrexone/Bupropion Contrave ®; Naltrexone SR/Bupropion SR, Adis R&D Profile, 10(1):25-32.
Aigner et al., 2011, World Federation of Societies of Biological Psychiatry Guideline for the Pharmacological Treatment of Eating Disorders, The world Journal of Biological Psychiatry, 12:400-443.
Albaugh et al., 2005, Topiramate prevents the rapid weight gain and adiposity in a model of atypical antipsychotic drug-induced obesity, Fed. of American Soc. For Experimental Biology, 19(5, Suppl. S, Part 2):A1130.

(Continued)

*Primary Examiner* — Kevin E Weddington
(74) *Attorney, Agent, or Firm* — Servilla Whitney LLC

(57) ABSTRACT

The present disclosure relates to compositions, kits, uses, systems and methods for treating overweight and obesity using naltrexone plus bupropion, preferably in combination with a comprehensive web-based and/or telephone-based weight management program, and preferably in subjects at increased risk of adverse cardiovascular outcomes.

20 Claims, 2 Drawing Sheets

(56) References Cited

U.S. PATENT DOCUMENTS

| | | |
|---|---|---|
| 5,856,332 A | 1/1999 | Dante |
| 5,866,164 A | 2/1999 | Kuczynski et al. |
| 5,948,799 A | 9/1999 | Cropp |
| 5,958,962 A | 9/1999 | Cook |
| 5,977,099 A | 11/1999 | Nickolson |
| 6,004,970 A | 12/1999 | O'Malley et al. |
| 6,033,686 A | 3/2000 | Seth |
| 6,034,091 A | 3/2000 | Dante |
| 6,048,322 A | 4/2000 | Kushida |
| 6,071,537 A | 6/2000 | Shank |
| 6,071,918 A | 6/2000 | Cook |
| 6,087,386 A | 7/2000 | Chen et al. |
| 6,096,341 A | 8/2000 | Seth |
| 6,110,973 A | 8/2000 | Young |
| 6,120,803 A | 9/2000 | Wong et al. |
| 6,143,327 A | 11/2000 | Seth |
| 6,150,366 A | 11/2000 | Arenson et al. |
| 6,153,223 A | 11/2000 | Apelian et al. |
| 6,183,778 B1 | 2/2001 | Conte et al. |
| 6,191,117 B1 | 2/2001 | Kozachuk |
| 6,197,827 B1 | 3/2001 | Cary |
| 6,210,716 B1 | 4/2001 | Chen et al. |
| 6,238,697 B1 | 5/2001 | Kumar et al. |
| 6,245,766 B1 | 6/2001 | Watsky |
| 6,248,363 B1 | 6/2001 | Patel et al. |
| 6,262,049 B1 | 7/2001 | Coffin et al. |
| 6,274,579 B1 | 8/2001 | Morgan et al. |
| 6,294,192 B1 | 9/2001 | Patel et al. |
| 6,306,436 B1 | 10/2001 | Chungi et al. |
| 6,323,236 B2 | 11/2001 | McElroy |
| 6,342,496 B1 | 1/2002 | Jerussi et al. |
| 6,342,515 B1 | 1/2002 | Masuda et al. |
| 6,344,474 B1 | 2/2002 | Maruani et al. |
| 6,362,220 B1 | 3/2002 | Cottrell |
| 6,369,113 B2 | 4/2002 | Young |
| 6,383,471 B1 | 5/2002 | Chen et al. |
| 6,387,956 B1 | 5/2002 | Shapira |
| 6,420,369 B1 | 7/2002 | Marcotte |
| 6,437,147 B1 | 8/2002 | Andersen et al. |
| 6,441,038 B1 | 8/2002 | Loder et al. |
| 6,451,860 B1 | 9/2002 | Young |
| 6,462,237 B1 | 10/2002 | Gidwani et al. |
| 6,500,459 B1 | 12/2002 | Chhabra et al. |
| 6,506,799 B1 | 1/2003 | Dasseux |
| 6,514,531 B1 | 2/2003 | Alaux et al. |
| 6,528,520 B2 | 3/2003 | Clemens |
| 6,541,478 B1 | 4/2003 | O'Malley et al. |
| 6,548,551 B2 | 4/2003 | Hinz |
| 6,569,449 B1 | 5/2003 | Stinchcomb et al. |
| 6,576,256 B2 | 6/2003 | Liang et al. |
| 6,589,553 B2 | 7/2003 | Li et al. |
| 6,622,036 B1 | 9/2003 | Suffin |
| 6,627,223 B2 | 9/2003 | Percel et al. |
| 6,630,165 B2 | 10/2003 | Seroff et al. |
| 6,638,535 B2 | 10/2003 | Lemmens et al. |
| 6,652,882 B1 | 11/2003 | Odidi et al. |
| 6,682,759 B2 | 1/2004 | Lim et al. |
| 6,686,337 B2 | 2/2004 | Connor |
| 6,706,283 B1 | 3/2004 | Appel et al. |
| 6,713,488 B2 | 3/2004 | Sadee et al. |
| 6,797,283 B1 | 9/2004 | Edgren et al. |
| 6,893,660 B2 | 5/2005 | Li et al. |
| 6,893,661 B1 | 5/2005 | Odidi et al. |
| 6,905,708 B2 | 6/2005 | Li et al. |
| 6,923,988 B2 | 8/2005 | Patel et al. |
| 6,926,907 B2 | 8/2005 | Plachetka |
| 6,995,169 B2 | 2/2006 | Chapleo et al. |
| 7,109,198 B2 | 9/2006 | Gadde et al. |
| 7,375,111 B2 | 5/2008 | Weber et al. |
| 7,422,110 B2 | 9/2008 | Zanden et al. |
| 7,425,571 B2 | 9/2008 | Gadde et al. |
| 7,429,580 B2 | 9/2008 | Gadde et al. |
| 7,462,626 B2 | 12/2008 | Weber et al. |
| 7,682,633 B2 | 3/2010 | Matthews et al. |
| 7,754,748 B2 | 7/2010 | Gadde et al. |
| 8,088,786 B2 | 1/2012 | McKinney et al. |
| 8,318,788 B2 | 11/2012 | McKinney et al. |
| 8,722,085 B2 | 5/2014 | McKinney et al. |
| 8,815,889 B2 | 8/2014 | Cowley et al. |
| 8,916,195 B2 | 12/2014 | McKinney et al. |
| 8,969,371 B1* | 3/2015 | Klassen ............... A61K 31/485 514/282 |
| 9,107,837 B2 | 8/2015 | McKinney et al. |
| 9,119,850 B2* | 9/2015 | Klassen ............... A61K 31/485 |
| 9,125,868 B2 | 9/2015 | McKinney et al. |
| 9,248,123 B2 | 2/2016 | Dunayevich et al. |
| 9,457,005 B2 | 10/2016 | Cowley et al. |
| 9,633,575 B2* | 4/2017 | Klassen ............... A61K 31/137 |
| 9,801,875 B2* | 10/2017 | Klassen ............... A61K 31/485 |
| 2001/0025038 A1 | 9/2001 | Coffin et al. |
| 2001/0046964 A1 | 11/2001 | Percel et al. |
| 2002/0012680 A1 | 1/2002 | Patel et al. |
| 2002/0019364 A1 | 2/2002 | Renshaw |
| 2002/0022054 A1 | 2/2002 | Sawada et al. |
| 2002/0025972 A1 | 2/2002 | Hintz |
| 2002/0037836 A1 | 3/2002 | Henriksen |
| 2002/0044962 A1 | 4/2002 | Cherukuri et al. |
| 2002/0055512 A1 | 5/2002 | Marin et al. |
| 2002/0090615 A1 | 7/2002 | Rosen et al. |
| 2002/0132850 A1 | 9/2002 | Bartholomaeus et al. |
| 2002/0198227 A1 | 12/2002 | Bernstein |
| 2003/0003151 A1 | 1/2003 | Chopra |
| 2003/0017189 A1 | 1/2003 | Wong et al. |
| 2003/0035840 A1 | 2/2003 | Li et al. |
| 2003/0044462 A1 | 3/2003 | Subramanian et al. |
| 2003/0054031 A1 | 3/2003 | Li et al. |
| 2003/0054041 A1 | 3/2003 | Lemmens et al. |
| 2003/0055008 A1 | 3/2003 | Marcotte |
| 2003/0055038 A1 | 3/2003 | Howard et al. |
| 2003/0068371 A1 | 4/2003 | Oshlack et al. |
| 2003/0087896 A1 | 5/2003 | Glover |
| 2003/0091630 A1 | 5/2003 | Louie-Helm et al. |
| 2003/0109546 A1 | 6/2003 | Fenton |
| 2003/0130322 A1 | 7/2003 | Howard |
| 2003/0133982 A1 | 7/2003 | Heimlich et al. |
| 2003/0133985 A1 | 7/2003 | Louie-Helm et al. |
| 2003/0135056 A1 | 7/2003 | Anderson et al. |
| 2003/0144174 A1 | 7/2003 | Brenna et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0005368 A1 | 1/2004 | Mann et al. |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1 | 10/2004 | Briggs et al. |
| 2004/0228915 A1 | 11/2004 | Noack et al. |
| 2004/0228924 A1 | 11/2004 | Oshlack et al. |
| 2004/0242974 A1 | 12/2004 | Glover |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |
| 2005/0019409 A1 | 1/2005 | Edgren et al. |
| 2005/0019412 A1 | 1/2005 | Bosch et al. |
| 2005/0026977 A1 | 2/2005 | Jennings |
| 2005/0026986 A1 | 2/2005 | Maruani et al. |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |

(56) References Cited

U.S. PATENT DOCUMENTS

| | | |
|---|---|---|
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0169990 A1 | 8/2005 | Kao et al. |
| 2005/0181049 A1 | 8/2005 | Dong et al. |
| 2005/0214368 A1 | 9/2005 | Kawakami et al. |
| 2005/0214371 A1 | 9/2005 | Di Capua et al. |
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Gadde et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0051418 A1 | 3/2006 | Cowen et al. |
| 2006/0058293 A1 | 3/2006 | Weber et al. |
| 2006/0069086 A1 | 3/2006 | Michalow |
| 2006/0079501 A1 | 4/2006 | Gadde et al. |
| 2006/0100205 A1 | 5/2006 | Weber et al. |
| 2006/0122127 A1 | 6/2006 | Rao et al. |
| 2006/0160750 A1 | 7/2006 | Gadde et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0099947 A1 | 5/2007 | Dean et al. |
| 2007/0117827 A1 | 5/2007 | Tollefson et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2008/0214592 A1 | 9/2008 | Cowley et al. |
| 2009/0018115 A1 | 1/2009 | Gadde et al. |
| 2009/0076108 A1 | 3/2009 | Gadde et al. |
| 2010/0166889 A1 | 7/2010 | Sanfilippo |
| 2010/0190793 A1 | 7/2010 | Weber et al. |
| 2011/0028505 A1 | 2/2011 | McKinney et al. |
| 2011/0098289 A1 | 4/2011 | Gadde et al. |
| 2011/0144145 A1 | 6/2011 | Tollefson |
| 2012/0010232 A1 | 1/2012 | Weber et al. |
| 2013/0177602 A1 | 7/2013 | McKinney et al. |
| 2013/0245056 A1 | 9/2013 | Flanagan |
| 2013/0252995 A1 | 9/2013 | Dunayevich et al. |
| 2014/0080857 A1 | 3/2014 | McKinney et al. |
| 2014/0364468 A1 | 12/2014 | Gadde et al. |
| 2015/0119417 A1 | 4/2015 | Tollefson |
| 2015/0141452 A1 | 5/2015 | Weber et al. |
| 2015/0164806 A1 | 6/2015 | McKinney et al. |
| 2016/0143903 A1 | 5/2016 | Dunayevich et al. |
| 2016/0158221 A1 | 6/2016 | McKinney et al. |
| 2016/0158225 A1 | 6/2016 | McKinney et al. |
| 2016/0193152 A1 | 7/2016 | McKinney et al. |
| 2016/0310485 A1 | 10/2016 | Klassen et al. |
| 2016/0338965 A1 | 11/2016 | McKinney et al. |
| 2016/0354348 A1 | 12/2016 | McKinney et al. |
| 2017/0007598 A1 | 1/2017 | Weber et al. |
| 2017/0014404 A1 | 1/2017 | McKinney et al. |
| 2017/0020990 A1 | 1/2017 | Cowley et al. |
| 2017/0172999 A1 | 6/2017 | Tollefson et al. |
| 2017/0312269 A1 | 11/2017 | McKinney et al. |

FOREIGN PATENT DOCUMENTS

| | | |
|---|---|---|
| EP | 0 294 028 | 12/1988 |
| EP | 0 442 769 | 8/1991 |
| EP | 0 541 192 | 5/1993 |
| EP | 0 598 309 | 5/1994 |
| EP | 1 275 373 | 1/2003 |
| EP | 1 772 147 | 4/2007 |
| EP | 1 759 701 | 7/2007 |
| EP | 1 813 276 | 8/2007 |
| JP | 2003-502358 | 1/2003 |
| JP | 2003-509349 | 3/2003 |
| JP | 2006-232675 | 9/2006 |
| RU | 2197250 C2 | 1/2003 |
| RU | 2214241 | 10/2003 |
| RU | 2342195 C1 | 12/2008 |
| WO | WO 83/03197 | 9/1983 |
| WO | WO 90/13294 | 11/1990 |
| WO | WO 94/20100 | 9/1994 |
| WO | WO 96/09047 | 3/1996 |
| WO | WO 97/06786 | 2/1997 |
| WO | WO 97/06787 | 2/1997 |
| WO | WO 97/41873 | 11/1997 |
| WO | WO 98/00130 | 1/1998 |
| WO | WO 99/16375 | 4/1999 |
| WO | WO 99/37305 | 7/1999 |
| WO | WO 99/38504 | 8/1999 |
| WO | WO 00/050020 | 8/2000 |
| WO | WO 00/51546 | 9/2000 |
| WO | WO 00/61139 | 10/2000 |
| WO | WO 00/062757 | 10/2000 |
| WO | WO 00/76493 | 12/2000 |
| WO | WO 01/01973 | 1/2001 |
| WO | WO 01/26641 | 4/2001 |
| WO | WO 01/52833 | 7/2001 |
| WO | WO 01/52851 | 7/2001 |
| WO | WO 01/058447 | 8/2001 |
| WO | WO 01/58451 | 8/2001 |
| WO | WO 01/058451 | 8/2001 |
| WO | WO 01/62257 | 8/2001 |
| WO | WO 01/78725 | 10/2001 |
| WO | WO 01/85257 | 11/2001 |
| WO | WO 02/09694 | 2/2002 |
| WO | WO 02/24214 | 3/2002 |
| WO | WO 02/087590 | 11/2002 |
| WO | WO 03/013524 | 2/2003 |
| WO | WO 03/013525 | 2/2003 |
| WO | WO 03/013479 | 3/2003 |
| WO | WO 03/045355 | 6/2003 |
| WO | WO 03/092682 | 11/2003 |
| WO | WO 03/097051 | 11/2003 |
| WO | WO 04/002463 | 1/2004 |
| WO | WO 04/009015 | 1/2004 |
| WO | WO 04/024096 | 3/2004 |
| WO | WO 04/052289 | 6/2004 |
| WO | WO 04/054570 | 7/2004 |
| WO | WO 04/054571 | 7/2004 |
| WO | WO 04/060355 | 7/2004 |
| WO | WO 04/071423 | 8/2004 |
| WO | WO 04/091593 | 10/2004 |
| WO | WO 04/100956 | 11/2004 |
| WO | WO 04/100992 | 11/2004 |
| WO | WO 04/110368 | 12/2004 |
| WO | WO 04/110375 | 12/2004 |
| WO | WO 05/000217 | 1/2005 |
| WO | WO 05/077362 | 2/2005 |
| WO | WO 05/032555 | 4/2005 |
| WO | WO 05/049043 | 6/2005 |
| WO | WO 05/079773 | 9/2005 |
| WO | WO 05/089486 | 9/2005 |
| WO | WO 06/049941 | 5/2006 |
| WO | WO 06/052542 | 5/2006 |
| WO | WO 06/055854 | 5/2006 |
| WO | WO 06/088748 | 8/2006 |
| WO | WO 07/012064 | 1/2007 |

(56) References Cited

FOREIGN PATENT DOCUMENTS

| WO | WO 07/024700 | 3/2007 | |
|---|---|---|---|
| WO | WO 07/047351 | 4/2007 | |
| WO | WO 07/85637 | 8/2007 | |
| WO | WO 08/119978 | 10/2008 | |
| WO | WO-2009158114 A1 * | 12/2009 | ........... A61K 31/137 |
| WO | WO 11/119953 | 9/2011 | |
| WO | WO 12/070043 | 5/2012 | |
| WO | WO 13/184837 | 12/2013 | |

OTHER PUBLICATIONS

Alger et al., Apr. 1991, Effect of a tricyclic antidepressant and opiate antagonist on binge-eating behavior in normoweight bulimic and obese, binge-eating subjects, The American Journal of Clinical Nutrition, 53(4):865-871.

Altman et al., 2005, Standard Deviations and Standard Errors, BMJ, 331:903.

Altomonte et al., 1988, Effect of fenfluramine on insulin/growth hormone ratio in obese subjects, Pharmacology, 36(2):106-111.

Anderson et al., 2002, Bupropion SR enhances weight loss: a 48-week double-blind, placebo-controlled trial, Obesity R., 10(7):633-641.

Appolinario et al., 2004, Pharmacological Approaches in the Treatment of Binge Eating Disorder, Current Drug Targets, 5:301-307.

Aronne et al., 2003, Weight gain in the treatment of mood disorders, J. Clin Psychiatry, 64(suppl 8).

Asconape, 2002, Some Common Issues in the Use of Antiepileptic Drugs, Seminars in Neurology; 22(1):27-39.

Astrup et al., Mar. 1991, Thermogenic Synergism Between Ephedrine and Caffeine in Healthy Volunteers: A Double-Blind, Placebo-Controlled Study, Metabolism, 40(3):323-329.

Atkinson et al. (Oct. 1985) Effects of long-term therapy with naltrexone on body weight in obesity, Clinical Pharmacology & Therapeutics, 38:419-422.

Atkinson, 2003, Clinical Guidelines on the identification, Evaluation, and pharmacologic treatment of obesity in Adults, Online, 07-25, URL:http://www.endotext.org.obesity/obesity15b/obesity15b.htm.

Atlantis et al., Oct. 6, 2009, Obesity and depression or anxiety, BMJ 2009:339:B3868.

Ayala (2000) Weight Loss Associated With the Administration of Zonisamide, AES Proceedings, Epilepsia 41(Suppl. 7) :99—No. 2.041.

Ayala et al., Dec. 1-6, 2000, Weight loss associated with the administration of zonisamide, a compendium of posters and platform session for ZonegranTM and Diastat®, Annual Meeting 2000 of the American Epilepsy Society, Los Angeles, CA.

Bakris et al., 2002, Orlistat improves blood pressure and control in obese subjects with treated but inadequately controlled hypertension, Journal of Hypertension, 20(11):2257-2267.

Baldassano et al. (2006) Acute treatment of bipolar depression with adjunctive zonisamide: a retrospective chart review, Disorders 6:432-434.

Barr et al. 1993. The serotonin hypothesis of obsessive compulsive disorder. International Clinical Psychopharmacology, 8(2):79-82.

Bastani et al. 1991. Serotonin uptake and imipramine binding in the blood platelets of obsessive-compulsive disorder patients. Biol. Psychiatry, 30:131-139.

Bays et al., Aug. 1, 2007, Adiposopathy: treating pathogenic adipose tissue to reduce cardiovascular disease risk, Current Treatment Options in Cardiovascular Medicine, 9(4):259-271.

Beelen et al. (2001) Asymptomatic QTC prolongation associated with queitiapine fumarate overdose in a patient being treated with risperidone, Human & Experimental Toxicology 20:215-219.

Bengtsson, 1993, The consequences of growth hormone deficiency in adults, Acta Endocrinol. (Copenh.), 128(Suppl 2):2-5.

Benjamin et al. 1993. Naltrexone and fluoxetine in Prader-Willi syndrome. J. Am. Acad. Child Adolesc. Psychiatry, 32(4):870-873.

Bergeron et al. 2002. Sertraline and fluoxetine treatment of obsessive-compulsive disorder: Results of a double-blind, 6-month treatment study. Journal of Clinical Psychopharmacology, 22(2):148-154.

Berke et al. (Jul. 15, 2000) Medical Management of Obesity, American Academy of Family Physicians, 62(2):419-26 Abstract.

Billett et al. 1997. Obsessive compulsive disorder, response to serotonin reuptake inhibitors and the serotonin transporter gene. Molecular Psychiatry, 2:403-406.

Blanchard et al. (2003) Pancreatitis Treated with Didanosine and Tenofabir Disoproxil Fumarate Clinical Infectious Diseases, 37:57-62.

Bradley et al., Aug. 2002, Bupropion SR versus placebo: comparison of depressive symptoms and weight loss in obese patients with a history of major depression, International Journal of Obesity, 26(Suppl. 1):S156.

Broocks et al. 1998. Higher prevalence of obsessive-compulsive symptoms in patients with blepharospasm than in patients with hemifacial spasm. Am. J. Psychiatry, 155:555-557.

Brown et al., 2012, Current and emerging directions in the treatment of eating disorders, Substance Abuse: Research and Treatment, 6:33-61.

Brunk, Sep. 1, 2009, Significant weight loss shown with naltrexone/bupropion combo, Thoracic Surgery News, http://www.thoracicsurgerynews.com/?id=95937&tx_ttnews[tt_news]=86987&cHash=a97b7f3c0f6a8c6a3b3ca96df9a6b73f, 1 pp.

Bupropion (Oral Route), MayoClinic.com, 19 pp., 2009.

Calabrese et al. (Sep. 2000) Letters to the Editors, Lamotrigine and Clozapine for Bipolar Disorder, American J. of Psychiatry, 157:1523.

Campana et al., Jan. 2005, P.6.034 Naltrexone and cravings: does it work with eating disorders?, European Neuropsychopharmacology, 15:S283.

Carlsen et al. (Jan. 1998) Evidence for dissociation of insulin-and weight-reducing effects of metformin in non-diabetic male patients with coronary heart disease, Diabetes Research and Clinical Practice Amsterdam, 39(1):47-54.

Carpenter et al. (Jan. 1, 1999) Mirtazapine Augmentation in the Treatment of Refractory Depression, J Clin Psychiatry, 60:1.

Carrion, 1995. Naltrexone for the treatment of trichotillomania: A case report. J. Clin. Psychopharmacol., 15(6):444-445.

Carroll (2003) Medicinal Chemistry Division Award Address: Monoamine Transporters and Opioid Receptors. Targets for Addiction Therapy, J. Med. Chem; 46(10):1775-1794.

Carson et al., May 1996, Pilot study of the use of naltrexone to treat the severe pruritis of cholestatic liver disease, Amer. J. Gastroenterology, 91(5):1022-1023.

Carter et al. 2003. Pharmacologic treatment of binge-eating disorder, The International Journal of Eating Disorders, 34(Suppl):S74-S88.

Carter et al. 2003. Pharmacologic treatment of binge-eating disorder. Primary Psychiatry, 10(10)31-36.

Casado et al., Apr. 2003, Sibutramine decreases body weight gain and increases energy expenditure in obese Zucker rats without changes in NPY and orexins, Nutr Neurosci, 6(2):103-111 (abstract).

Cash et al. (2000) Attitudes about antidepressants: Influence of information about weight-related side effects, Perceptual and Motor Skills, 90:453-456.

Casner et al. 1996. Naltrexone and self-injurious behavior: A retrospective population study. Journal of Clinical Psychopharmacology, 16(5):389-394.

Chakraborty et al., 2010, Management of anorexia and bulimia nervosa: an evidence-based review, Indian J Psychiatry, 52:174-186.

Chen et al. (Jan. 2004) Synergistic Effects of Cannabinoid inverse agonist AM251 and opioid antagonist nalmefene on food intake, Brain Res, 999:22-230.

Chen et al., 2005, Combination treatment of clozapine and No Suggestions) in resistant rapid-cycling bipolar disorder, Clin. Neuropharmacol. 28(3):136-138.

Chen et al., Jun. 2003, Nonketotic hyperosmolar syndrome from olanzapine, lithium, and valproic acid cotreatment, Annals of Pharmacotherapy, 37(6):919-920.

(56) References Cited

OTHER PUBLICATIONS

Chengappa et al. (2002) Changes in body Weight and Body mass index among psychiatric patients receiving lithium, valproate, or topiramate: an open-label, nonrandomized chart review, Clinical Therapeutics, 24(10):1576-1584.
Ching, Mar. 1980, Influence of diphenylhydantoin upon oral glucose tolerance test in obesity, Chinese Medical Journal, 27(1):432-439.
Chouinard et al. 1996. Potentiation of fluoxetine by aminoglutethimide, an adrenal steroid suppressant, in obsessive-compulsive disorder resistant to SSRIs: A case report. Prog. Neuro-Psychopharmacol. & Biol. Psychiat., 20:1067-1079.
Clapham et al. (2001) Anti-obesity drugs: a critical review of current therapies and future opportunities. Pharmacology & Therapeutics. 89:81-121.
Clark et al., 2003, Diabetes mellitus associated with atypical antipsychotic medications, Diabetes Technology & Therapeutics, 5(4):669-683.
Cleveland Clinic Press Release: "Clinical Trial Testing Safety of Obesity Drug Contrave Halted; 50 Percent Interim Data Released by the Study's Executive Committee", May 12, 2015, retrieved from http://my.clevelandclinic.org/about-cleveland-clinic/newsroom/releases-videos-newsletters/2015-5-12-clinical-trial-testing-safety-of-obesity-drug-contrave-halted.
Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.
Clinical Trials.gov, A Multicenter, randomized, double-blind, placebo-controlled study assessing the occurrence of major adverse cardiovascular events (MACE) such as cardiovascular death, non-fatal myocardial infarction, and non-fatal stroke in overweight and obese subjects who are at a higher risk of having these events because they have diabetes and/or other cardiovascular risk factors, NTC01601704, May 7, 2013, 4 pp.
Clinical Trials.gov, Jul. 13, 2009, An open-label study assessing the safety and efficacy of naltrexone sustained release (SR)/bupropion sustained release (SR) in overweight or obese subjects with major depression, 2 pp.
ClinicalTrials.gov archive, Apr. 21, 2008, A phase 3 study comparing the safety and efficacy of naltrexone sr/bupropion sr and placebo in obese subjects with type 2 diabetes mellitus, 3 pp.
ClinicalTrials.gov archive, Feb. 5, 2010, A phase 3 study comparing the safety and efficacy of two doses of naltrexone sustained release (SR)/bupropion sustained release (SR) and placebo in obese subjects, NCT00532779, 3 pp.
ClinicalTrials.gov archive, May 2012, Cardiovascular outcomes study of Naltrexone SR/Bupropion SR in overweight and obese subjects with cardiovascular risk factors (the light study), 4 pp.
ClinicalTrials.gov, Apr. 3, 2007, A safety and efficacy study of naltrexone sr/bupropion sr and placebo in overweight and obese subjects participating in an intensive behavior modification program, NCT00456521, 5 pp.
Colosimo et al., 1999, Motor fluctuations in Parkinson's disease: pathophysiology and treatment, European Journal of Neurology, 6:1-21.
Cone et al. (2001) The arcuate nucleus as a conduit for diverse signals relevant to energy homeostasis, Int'l Journal of Obesity, 25(5):S63-S67.
Croft et al. (Apr. 2002) Effect on body weight of bupropion sustained-release in patients with major depression treated for 52 weeks, Clinical Therapeutics 24(4):662-672.
Cunningham, May 1963, Diethylpropion in the treatment of obesity, The Journal of the College of General Practitioner, 6(2):347-349.
Cuparencu et al., 1993, Effects of some benzodiazepines on glycemia in albino rats, Romanian Journal of Physiology, 30(1-2):7-15 (abstract).
Das et al., 2003, Controlled-release of oral dosage forms, Formulation, Fill & Finish, pp. 10-16.
De Boer et al., 1995, Clinical aspects of growth hormone deficiency in adults, Endocrine Reviews, 16(1):63-86.
Dechant et al., 1991, Paroxetine: a review of its pharmacodynamic and pharmacokinetic properties, and therapeutic potential in depressive illness, Drugs, 41:225-253.
Defendant Actavis Laboratories FL, Inc.'s Initial Invalidity Contentions for U.S. Pat. No. 9,125,868, in Takeda Pharmaceutical Company Limited et al., *Plaintiffs*, v. *Actavis Laboratories FL, Inc.*, Defendant, C.A. No. 15-451-RGA, US District Court for the District of Delaware, dated Jul. 25, 2016, 48 pp.
Defendant Actavis Laboratories FL, Inc.'s Initial Invalidity Contentions for U.S. Pat. Nos. 7,375,111, 7,462,626, and U.S. Pat. No. 8,916,195, in Takeda Pharmaceutical Company Limited et al., *Plaintiffs*, v. *Actavis Laboratories FL, Inc.*, Defendant, C.A. No. 15-451-RGA, US District Court for the District of Delaware, dated Dec. 23, 2015, 147 pp.
Dembowski et al. (2003) Successful Antimanic Treatment and Mood Stabilization with Lamotrigine, Clozapine, and Valproate in a Bipolar Patient after Lithium-induced Cerebellar Deterioration, Letter Pharmacopsychiatry, 36:83-86.
Deshmukh et al. (Jul. 2003) Managing weight gain as a side effect of antidepressant therapy, Cleveland Clinic Journal of Medicine, 70(7):614-623.
DeSimone et al. (2005) Carbonic anhydrase inhibitors. Zonisamide is an effective inhibitor of the cytosolic isozyme II and mitochondrial isozyme V: Solution and x-ray crystallographic studies, Bioorganic & Medicinal Chemistry Letters, 15:2315-2320.
Devlin et al. (2000) Open treatment of overweight binge eaters with phentermine and fluoxetine as an adjunct to cognitive-behavioral therapy. Int. J. Eating Disord; 28:325-332.
Dramatic alcohol treatment results seen with naltrexone, Psychiatric Times, Sep. 1, 1998, 5 pp.
Drugs.com, Sep. 20, 2011, Orexigen and FDA identify a clear and feasible path to approval for contrave, http://www.drugs.com/nda/contrave_110920.html, 4 pp.
Durgin et al., 2005, Pharmaceutical Practice for Technicians, 3rd Edition, Thomson Delmar Learning, p. 174.
Dursun et al. (2001) Accelerated Weight Loss After Treating Refractory Depression with Fluoxetine Plus Topiramate: Possible Mechanism of Action, Canadian Journal of Psychiatry, 46(3):287-288.
Dursun et al. (2001) Augmenting Antipsychotic treatment with Lamotrigine or topiramate in patients with treatment-resistant Schizophrenia: a naturalistic case-series outcome study Journal of Psychopharmacology 15(4):297-301.
Dursun et al. (2001) Psychopharmacology for the Clinician Psychopharmacologie Pratiqu, Journal of Psychiatry Neuroscience, 26(2):168.
Dursun et al. (Oct. 1999) Clozapine Plus Lamotrigine in Treatment-Resistant Schizophrenia, Arch Gen Psychiatry, 56:950-951.
Dwyer et al., 2002, Psychoactive drugs affect glucose transport and the regulation of glucose metabolism, International Review of Neurobiology, 51:503-530.
Eckel et al., Apr. 16, 2005, The metabolic syndrome, The Lancet 365:1415-1428.
Eid et al., 2005, Effective treatment of polycystic ovarian syndrome with roux-en-y gastric bypass, Surgery for Obesity and Related Diseases, 1:77-80.
El-Haschimi et al. 2000. Two defects contribute to hypothalamic leptin resistance in mice with diet-induced obesity. The Journal of Clinical Investigation, 105(12):1827-1832.
Erez et al., 1982, Narcotic antagonistic potency of bivalent ligands which contain β-naltrexamine. Evidence for bridging between proximal recognition sites, J. Med. Chem., 25:847-849.
Erfurth et al., Mar. 2002, Bupropion as add-on strategy in difficult-to-treat bipolar depressive patients, Neurophsychobiology, 45(Supplement 1):33-36.
Erzegovesi et al. 2001. Clinical predictors of drug response in obsessive-compulsive disorder. Journal of Clinical Psychopharmacology, 21(5):488-492.
Esposito-Avella et al. (Jan. 1973) Studies on the protective effect of diphenylhyndantoin against alioxan diabetes in mice, Proceedings of the Society for Experimental Biology & Medicine, 142(1):82-85.
Ettmayer et al, May 6, 2004, Lessons learned from marketed and investigational prodrugs, J. Med. Chem, 47(10):2393-2404.

(56) References Cited

OTHER PUBLICATIONS

Faught et al. (2001) Randomized Controlled Trial of Zonisamide for the Treatment of Refractory Partial-Onset Seizures., Neurology; 57(10):1774-1779.
Fava, 2000, Weight Gain and Antidepressants. J Clin Psychiatry; 61(suppl 11):37-41.
Ferre et al. (1996) Correction of diabetic alterations by glucokinase. Proc. Natl. Acad. Sci. USA, 93:7225-7230.
Ferre et al. (1996) Evidence from transgenic mice that glucokinase is rate limiting for glucose utilization in the liver, The FASEB Journal, 10:1213-1218.
Fingl et al., The Pharmacological Basis of Therapeutics. Chapter 1: General Principles, pp. 1-46 (1975).
Fontela et al., Mar. 1986, Blocking effect of naloxone, dihydroergotamine and adrenalectomy in lithium-induced hyperglycaemia and glucose intolerance in the rat, Acta Endocrinologica, 111(3):342-348 (abstract).
Fujioka et al., Jan. 1987, Contribution of intra-abdominal fat accumulation to the impairment of glucose and lipid metabolism in human obesity, Metabolism, 36(1):54-59.
Fukagawa et al. (Nov. 2001) Monoaminergic anorectic agents, Nippon Yikurigaku Zasshi, 118(5):303-8, 2001 Abstract.
Fulghesu et al. (Aug. 1993) Long-term naltrexone treatment reduces the exaggerated insulin secretion in patients with polycystic ovary disease, Obstetrics & Gynecology, 82(2):191-197.
Fuller et al. (1989) Fluoxetine: A Serotonergic Appetite Suppressant Drug, Drug Development Research, 17(1):1-15.
Gadde et al, "Zonisamide in Obesity: A 16-Week Randomized Trial", No. NR473, New Research, American Psychiatric Association 2002 Annual Meeting, May 18-23, 2002, Philadelphia, Pennsylvania (abstract).
Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.
Gadde et al. "Bupropion for Weight Loss: An Investigation of Efficacy and Tolerability in Overweight and Obese Women" Obesity Research 9(9):544-551 (2001).
Gadde et al. , "Zonisamide for Weight Loss in Obese Adults—A Randomized Controlled Trial" JAMA 289 (14): 1820-1825 (2003).
Gadde et al., 2002, Randomized controlled trial of zonisamide for treating obesity, Epilepsia 43 Suppl. 7:218 (abstract).
Gadde et al., 2003, Zonisamide enhances weight loss in patients with obesity. Inpharma, 1383(84):9.
Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.
Gadde et al., Sep. 1999, A randomized double-blind placebo-controlled study of bupropion sustained release in obesity, European Neuropsychopharmacology, 9(5):366.
Gatley et al.,1996, 123I-labeled AM251 : a radioiodinated ligand which binds in vivo to mouse brain cannabinoid Cb1 receptors. European Journal of Pharmacology; 307:331-338.
Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.
Gerich et al. (1972) In vitro inhibition of pancreative glucagon secretion by diphenylhydantoin, Journal of Clinical Endocrinology and Metabolism 35(6):823-824.
Gerra et al. 1995. Hostility in heroin abusers subtypes: Fluoxetine and naltrexone treatment. Prog. Neuro-Psychopharmacol. & Biol. Psychiat., 19:1225-1237.
Gerra et al., Sep. 30, 2006, Effects of olanzapine on aggressiveness in heroin dependent patients, Progress in Neuro-Psychopharmacology & Biological Psychiatry, 30(7):1291-1298.
Ghisoli et al., 1980, Effects of dopaminergic receptor stimulation and opioid receptor blockade on GH incretion: preliminary findings, Boll. Soc. Ital. Biol. Sper., 56(12):1222-1225.
Ghisoli et al., 1980, Effects of interaction between 2-Br-α-ergocryptine (CB 154) and naloxone on the control of insulin secretion in normal man, Boll. Soc. Ital. Biol. Sper., 56(12):1215-1221.
Ginsberg et al. (2000) Effects of Mood Stabilizers on Weight, Primary Psychiatry 7(5):49-58.
Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.
Glass et al., 1999, Opioids and food intake: distributed functional neural pathways?, Neuropeptides, 33(5):360-368.
GlaxoSmithKline, Jun. 2009, Prescribing Information: Wellbutrin® (bupropion hydrochloride) Tablets, pp. 4-32.
Glod et al., Jul.-Sep. 2003, Open trial of bupropion sr in adolescent major depression, J Child Adolesc Psychiatr Nurs, 16(3):123-130.
Goldstein et al. (Mar. 1994) Fluoxetine: a randomized clinical trial in the treatment of obesity, International Journal of Obesity and Related Metabolic Disorders, 17(3):129-135, CAS accession #9424430.
Goodman & Gillman's, The Pharmacological Basis of Therapeutics, 10th Ed., Edited by J. Hardman and L. Limbird, 2001, p. 6.
Goodman et al. 1989. The Yale-Brown obsessive compulsive scale. Arch. Gen. Psychiatry, 46:1006-1011.
Goodpaster et al., Feb. 2003, Association between regional adipose tissue distribution and both type 2 diabetes and impaired glucose tolerance in elderly men and women, Diabetes Care, 26(2):372-379.
Gordon et al. (Jun. 1999) Mood Stabilization and Weight Loss with Topiramate American Journal of Psychiatry, American Psychiatric Association, Washington D.C., 156(6):968-969.
Gormally et al., 1982, The assessment of binge eating severity among obese persons, Addict Behav, 7(1):47-55.
Grady (Mar. 15, 2003) Quest for Weight-Loss Drug Takes an Unusual Turn, The New York Times—Health, www.nytimes.com, 3 pp.
Grant et al. 2004. Impulse control disorders: Clinical characteristics and pharmacological management. Annals of Clinical Psychiatry, 16:27-34.
Grant et al. 2004. Pharmacotherapy outcome in older pathological gamblers: A preliminary investigation. Journal of Geriatric Psychiatry and Neurology, 17(1):9-12.
Grant et al. 2006. Compulsive aspects of impulse-control disorders. Psychiatr. Clin. North Am., 29(2):539-x.
Greenberg et al. 1998. Delayed obsessive-compulsive disorder symptom exacerbation after a single dose of a serotonin antagonist in fluoxetine-treated but not untreated patients. Psychopharmacology, 140:434-444.
Greenway et al. (2002) A Long-acting Leptin Analog does not Enhance Fat, Visceral Fat, or Weight Loss When Combined with Caffeine Ephedrine in Obese Subjects, International Journal of Obesity, S136.
Greenway et al. (Jul. 1999) Double-Blind, Randomized, Placebo-Controlled Clinical Trials with Nonprescription Medications for the Treatment of Obesity', Obesity Research, 7(4):370-78.
Greenway et al., Dec. 2009, Comparison of combined bupropion and naltrexone therapy for obesity with monotherapy and placebo, J. Clin Endocrinol Metab, 94(12):4898-4906.
Greenway et al., Jan. 2009, Rational design of a combination medication for the treatment of obesity, Obesity, 17(1):30-39.
Greenway et al., Jun. 10, 2008, Naltrexone and bupropion reduce the prevalence of the metabolic syndrom, Diabetes, 57(Suppl. 1), Abstract No. 2735-PO.
Greenway et al., Jun. 2006, Bupropion and naltrexone for the treatment of obesity, Diabetes: Abstract Book: 66th Scientific Sessions, 55(Supplement 1):A395.
Greenway et al., Jun. 2006, Bupropion and naltrexone for the treatment of obesity, poster, 1 pg.
Greenway et al., Oct. 22, 2010, Effect of naltrexone plus bupropion on weight loss in overweight and obese adults (COR-I): a multicentre, randomized, double-blind, placebo-controlled, phase 3 trial, Lancet, 376:595-605.
Greist et al. (Apr. 1995) Double-blind Parallel Comparison of Three Dosages of Sertraline and Placebo in Outpatients With Obsessive-compulsive Disorder, Arch Gen Psychiatry, 52:289-295.

(56) References Cited

OTHER PUBLICATIONS

Grundy et al., 2005, Diagnosis and management of the metabolic syndrome, Circulation, 112:2735-2752.
Grunenthal, Neo-Eunomin Gebrauchsinformation, Neunomin Prescription Information, Feb. 2004, pp. 1-2.
Guidance for Industry Estimating the Maximum Safe Starting Dose in Initial Clinical Trials for Therapeutics in Adult Healthy Volunteers, U.S. Department of Health and Human Services, U.S. Food and Drug Administration Center for Drug Evaluation and Research (CDER), Pharmacology and Toxicology, Jul. 2005.
Hagan et al., Dec. 1997, Combined naloxone and fluoxetine on deprivation-induced binge eating of palatable foods in rats, Pharmacol Biochem Behav, 58(4):1103-1107.
Hahn et al. (1985) Irreversible opiate agonists and antagonists. III. Phenylhydrazone derivatives of naloxone and oxymorphone. J. Pharm. Exper. Therapeutics; 235:846-850.
Halford et al., May 2010, Pharmacological management of appetite expression in obesity, Nature Reviews Endocrinology, 6(5):255-269.
Halpern et al., Jul. 27, 2010, Combinations of drugs in the treatment of obesity, Pharmaceuticals, 3:2398-2415.
Hamidi et al. 2007. Naltrexone in obsessive-compulsive disorder: an open-label trial. Iranian Journal of Psychiatry and Behavioral Sciences, 1(1):16-21.
Harrison's Principles of Internal Medicine, Braunwald et al., The epilepsies and convulsive disorders, Eleventh Edition, McGraw-Hill Book Company, pp. 1921-1930 (1987).
Hashiguti et al. (1993) Simultaneous determination of in vivo hydroxylation of tyrosine and tryptophan in rat striatum by microdialysis-HPLC: relationship between dopamine and serotonin biosynthesis; Journal of Neural Transmission, 93:213-223.
Hausenloy, 2009, ContraveTM: Novel treatment for obesity, Clinical Lipidology, 4(3):279-285.
Herper, "A Top Cardiologist Says a Diet Drug Maker Misled Patients and Investors", Forbes, May 12, 2015, retrieved from http://www.forbes.com/sites/matthewherper/2015/05/12/a-top-cardiologist-says-a-diet-drug-maker-misled-patients-and-investors/#.
Herper, "Heart Benefit for Orexigen Drug Nearly Vanishes with New Data", Forbes, May 12, 2015, retrieved from http://www.forbes.com/sites/matthewherper/2015/05/12/heart-benefit-for-orexigen-drug-nearly-vanishes-with-new-data/.
Herper, Mar. 5, 2015, Top FDA Official Says Orexigen Study Result 'Unreliable,'"Misleading, http://www/forbes.com/sites/matthewherper/, 4 pp.
Hollander et al. 1991. Effects of chronic fluoxetine treatment on behavioral and neuroendocrine responses to meta-chlorophenylpiperazine in obsessive-compulsive disorder. Psychiatry Research, 36:1-17.
Hollander et al., Oct. 21, 2013, Effects of naltrexone sustained-release/bupropion sustained release combination therapy on body weight and glycemic parameters in overweight and obese patents with type 2 diabetes, Diabetes Care, 36(12):4022-4029.
Horne et al., Jul. 1988, Treatment of bulimia with bupropion: a multicenter controlled trial, The Journal of Clinical Psychiatry, 49(7):262-266.
Hussey et al., 2002, Synthesis of a β-estradiol-biotin chimera that potently heterodimerizes estrogen receptor and streptavidin proteins in a yeast three-hybrid system, J. Am. Chem. Soc., 125:3692-3693.
Husten, Mar. 3, 2015, Orexigen Released Interim Data Without Approval of Trial Leaders, http://ww/forbes.com/sites/harryhusten, 6 pp.
Insulin Resistance and Pre-diabetes, http://diabetes.niddk.hih.gov/DM/pubs/insulineresistance/, NIH Publication No. 09/4893, Oct. 2008, 9 pp.
Ioannides-Demos et al., 2005, Pharmacotherapy for obesity, Drugs, 65(10):1391-1418.
Islam et al., 1994, Naltrexone, Serotonin Receptor Subtype Antagonists, and Carbohydrate Intake in Rats, Pharmacology Biochemistry and Behavior, 48(1):193-201.
Jain et al. (Oct. 2002) Bupropion SR vs. Placebo for Weight Loss in Obese Patients with Depressive Symptoms, Obesity Research, 10:1049-1056.
Jallon et al. (2001) Bodyweight gain and anticonvulsants: a comparative review. Drug Safety; 24(13):969-978.
Janssen et al., 1999, Effects of sex on the change in visceral, subcutaneous adipose tissue and skeletal muscle in response to weight loss, International Journal of Obesity, 23, pp. 1035-1046.
Japanese Journal of Clinical Psychiatry (1987 16(1):123-132), and English-language version of Japanese Office Action citing the same (dated Oct. 28, 2008).
Johannsson et al., 1997, Growth hormone treatment of abdominally obese men reduces abdominal fat mass, improves glucose and lipoprotein metabolism, and reduces diastolic blood pressure, J. Clin. Endocrin. and Metab., 82(3):727-734.
Johnson et al., Oct. 14, 2010, Food effects on the pharmacokinetics of morphine sulfate and naltrexone hydrochloride extended release capsules, Advances in Therapy, 27(11):846-858.
Johnston et al., 2002, Pharmacokinetic optimization of sustained-release bupropion for smoking cessation, Drugs, 62(Suppl. 2):11-24.
Jonas et al.., 1986, Treatment of binge-eating an open-study of naltrexone, Society for Neuroscience Abstracts, 12(1):595.
Jones et al., 2003, Effect of naltrexone on food intake and body weight in Syrian hamsters depends on metabolic status, Physiology & Behavior 28:67-72.
Kanba et al. (1994) The first open study of zonisamide, a novel anticonvulsant, shows efficacy in mania. Progress in Neuro-Psychopharmacology and Biological Psychiatry; 18(4):707-715.
Katsiki et al., Jun. 1, 2011, Naltrexone sustained-release (SR) + bupropion SR combination therapy for the treatment of obesity: 'A new kid on the block'?, Annals of Medicine, 43(4):249-258.
Kelley et al., 2000, A pharmacological analysis of the substrates underlying conditioned feeding induced by repeated opioid stimulation of the nucleus accumbens, Neuropsychopharmacology, 23(4):455-467.
Kelly et al., 2006, Adjunct divalproex or lithium to clozapine in treatment-resistant schizophrenia, Psychiatric Quarterly, 77(1):81-94.
Kennett et al., Nov. 2010, New approaches to the pharmacological treatment of obesity: can they break through the efficacy barrier?, Pharmacology Biochemistry and Behavior, 97(1):63-83.
Khaylis et al., Nov. 2010, A review of efficacious technology-based weight-loss interventions: five key components, Telemedicine and e-Health, 16(9):931-938.
Kim et al. 1990. Open fixed dose trial of fluoxetine in the treatment of obsessive compulsive disorder. Drug Development Research, 19:315-319.
Kimura et al., 1992, Pharmacokinetic interaction of zonisamide in rats: effects of other antiepileptics on zonisamide, J. Pharmacobio-Dyn. 15:631-639.
Kiptoo et al. (2006) Enhancement of Transdermal delivery or 6-B-naltrexol via a codrug linked to hydroxybupropion, Journal of Controlled Release 113:137-145.
Kirkham et al. (2001) Synergistic effects of opioid and cannabinoid antagonists on food intake. Psychopharmacology; 153:267-270.
Kirov et al. (2003) Add-on topiramate reduces weight in overweight patients with affective disorders: a clinical case. BMC Psychiatry, 5:19, 8 pp.
Kivimaki et al., Common mental disorder and obesity—insight from four repeat measures over 19 years: prospective Whitehall II cohort study, BMJ 2009; 339:b3765.
Klein et al., Jun. 1, 2009, Naltrexone plus bupropion combination causes significant weight loss without worsening psychiatric symptoms, Diabetes, 58(Suppl. 1):A444, Abstract 1739-P.
Klok et al., 2002, Cholesteryl-(l-lactic acid)n building blocks for self-assembling biomaterials, Macromolecules, 35:746-759.
Kolb et al. (1985) Synthesis and Pharmacological Characterization of Fluorescent Opioid Receptor Probes. A. Pharmaceutical Res, 2(6):266-271.
Korner et al. (2003) The emerging science of body weight regulation and its impact on obesity treatment, J. Clin. Invest. 111(5):565-570.

(56) References Cited

OTHER PUBLICATIONS

Kossard, et al. 2006. Defining urticarial dermatitis: A subset of dermal hypersensitivity reaction pattern. Arch. Dermatol., 142:29-34.
Krauss et al. 1997. Tics secondary to craniocerebral trauma, Movement Disorders, 12(5):776-782.
Kristeller et al., Jan. 12, 1999, An exploratory study of a meditation-based intervention for binge eating disorder, J. Health Psychol, 4(3):357-363.
Kruger, 2000, Psychopharmacotherapy of anorexia nervosa, bulimia nervosa and binge-eating disorder, J. Psychiatry Neurosci, 25(5):497-508.
Krupitsky et al. 2006. Naltrexone with or without fluoxetine for preventing relapse to heroin addiction in St. Petersburg, Russia. Journal of Substance Abuse Treatment, 31:319-328.
Kuk et al., 2006, Visceral fat is an independent predictor of all-cause mortality in men, Obesity, 14(2):336-341.
Kushner et al. (Mar. 2002) Obesity pharmacology: past, present, and future, Current Opinion in Gastroenterology, pp. 213-220.
Laessle et al., May 1997, A comparison of resting metabolic rate, self-rated food intake, growth hormone, and insulin levels in obese and nonobese preadolescents, Physiol. Behav., 61(5):725-729.
Landabaso et al. 1998. A randomized trial of adding fluoxetine to a naltrexone treatment programme for heroin addicts. Addiction, 93(5):739-744.
Le Bourdonnec et al., 2002, Reporter affinity labels: an o-phthalaldehyde derivative of β-naltrexamine as a fluorogenic ligand for opioid receptors, J. Med. Chem., 43(13):2489-2492.
Leppik (Dec. 2004) Zonisamide: chemistry, mechanism of action, and pharmacokinetics,Seizure, 13(Suppl 1):S5-9; discussion S10.
Leppik et al. (1993) Efficacy and safety of zonisamide: results of a multicenter study. Epilepsy Research; 14:165-173.
Lesch et al. 1991. Long-term fluoxetine treatment decreases 5-HT1A receptor responsivity in obsessive-compulsive disorder. Psychopharmacology, 105:415-420.
Lessig et al. (Dec. 2001) Topiramate for Reversing Atypical Antipsychotic Weight Gain, J. Am. Child Adolesc. Psychiatry 40(12):1364.
Levy et al. (Nov. 2002) Topiramate Produced Weight Loss Following Olanzapine-Induced Weight Gain in Schizophrenia, J. Clin. Psychiatry, 63(11):1045.
Levy et al. 1985. Utility of free level monitoring of antiepileptic drugs. Epilepsia, 26(3):199-205.
Lin et al. 2000. Development of high fat diet-induced obesity and leptin resistance in C57B1/6J mice. International Journal of Obesity, 24:639-646.
López-Ibor, Jr. et al. 1996. Double-blind comparison of fluoxetine versus clomipramine in the treatment of obsessive compulsive disorder. European Neuropsychopharmacology, 6:111-118.
Lowry, Feb. 2008, Study: bupropion-naltrexone combo best for weight loss, Clinical Psychiatric News, 1 pp.
Ludman et al., "Does depression reduce the effectiveness of behavioral weight loss treatment?" Behav Med. 2010; 35(4):126-134 (abstract).
Luppino et al., Mar. 2010, Overweight, obesity, and depression: a systematic review and meta-analysis of longitudinal studies, Arch Gen Psychiatry, 67(3):220-229.
Malcolm et al. (Jun. 1985) A Controlled Trial of Naltrexone in Obese Humans, International Journal of Obesity, 9:347-353.
Malhotra et al. (2002) Medical Management of Obesity Associated With Mental Disorders, Journal of Clinical Psychiatry, 63(suppl 4):24-32.
Marrazzi et al., Feb. 1995, Binge eating disorder: response to naltrexone, International Journal of Obesity, 19(2):143-145.
Matsuura (2000) Indication for Anterior Temporal Lobectomy in Patients with Temporal Lobe Epilepsy and Psychopathology, Epilepsia, 41(Suppl. 9):39-42.

McDougle et al. (Aug. 2000) A double-blind, placebo-controlled study of risperidone addition in serotonin reuptake inhibitor-refractory obsessive-compulsive disorder, Archive of General Psychiatry, 57(8):794-801.
McElroy et al. (2000) Pharmacologic agents for the treatment of acute bipolar mania, Biological Psychiatry, 48(6):539-557.
McElroy et al. (2004) Zonisamide in the Treatment of Binge-Eating Disorder: An Open-Label, Prospective Trial, J. Clin. Psychiatry, 65(1):50-56.
McElroy et al. (2004) Zonisamide is effective in the treatment of binge-eating disorder. Inpharma; 1428:10.
McElroy et al., Jun. 1, 2010, An open-label study evaluating the naltrexone SR/bupropion SR combination therapy in overweight or obese subjects with major depression, Diabetes, 59(Suppl. 1):A483.
McElroy et al., Jun. 2013, Naltrexone/bupropion combination therapy in overweight or obese patients with major depressive disorder: results of a pilot study, Prim Care Companion CNS Disord, 15(3), 17 pp.
McElroy et al., May 7, 2012, Pharmacological management of binge-eating disorder: current and emerging treatment options, Therapeutics and Clinical Risk Management, 8:219-241.
McElroy et al., Nov. 2010, Reduced depressive symptoms and weight loss in depressed overweight/obese subjects completing 24 weeks of open label therapy with naltrexone sr/bupropion sr, 18(Supp 2):S152.
McLaughlin et al. (2003) The cannabinoid CB1 antagonists SR 141716A and AM 251 suppress food intake and food-reinforced behavior in a variety of tasks in rats. Behavioral Pharmacology; 14:583:588.
McLaughlin et al., 1983, Nalmefene decreases meal size, food and water intake and weight gain in Zucker rats, Pharmacology Biochemistry and Behavior, 19(2):235-240 (abstract).
Melander, Oct. 1978, Influence of food on the bioavailability of drugs, Clinical Pharmacokinetics, 3(5):337-351.
Meyer et al., Sep. 1984, Bioequivalence, dose-proportionality, and pharmacokinetics of naltrexone after oral administration, J. Clin. Psychiatry, 45(9)(Sec. 2):15-19.
Meyer, Dec. 2008, Alleviation of both binge eating and sexual dysfunction with naltrexone, Journal of Clinical Psychopharmacology, 28(6):722-723.
Michelson et al. (Nov. 2001) Atomexetine in the Treatment of Children and Adolescents with Attention Deficit/Hyperactivity Disorder: A Randomized, Placebo-Controlled, Dose-Response Study, Pediatrics,108(5):E83 Abstract.
Midha et al., May 2005, Exposure measures applied to the bioequivalence of two sustained release formulations of bupropion, International Journal of Clinical Pharmacology and Therapeutics, 43(5):244-254.
Milano et al., May-Jun. 2005, Treatment of bulimia nervosa with fluvoxamine: a randomized controlled trial, Advances in Therapy, 22(3):278-283.
Millet et al. 1999. Obsessive-compulsive disorder: Evaluation of clinical and biological circadian parameters during fluoxetine treatment. Psychopharmacology, 146:268-274.
Mitchell et al. (1987) High-Dose Naltrexone Therapy and Dietary Counseling for Obesity, Biological Psychiatry, 22:35-42.
Miyazaki, 2005, Adiposity and Drug Treatment, Resident Notes, 7(4):499-502.
Monteleone et al. 1995. Plasma melatonin and cortisol circadian patterns in patients with obsessive-compulsive disorder before and after fluoxetine treatment. Psychoneuroendocrinology, 20(7):763-770.
Morris, III (Dec. 3, 2000) The Effect of Zonisamide Administration on Patient Weight, A Scientific Exhibit at the American Epilepsy Society Annual Meeting, Los Angeles, California.
Mukherjee, "UPDATE: Takeda threatens to break off Orexigen collab after Contrave data drama", BioPharmaDive, May 13, 2015, retrieved from http://www.biopharmadive.com/news/update-takeda-threatens-to-break-off-orexigen-collab-after-contrave-data-d/396940/.
Must et al. (Oct. 27, 1999) The disease burden associated with overweight and obesity, JAMA, 282(16):1523-1529.

(56) References Cited

OTHER PUBLICATIONS

Najim et al., Dec. 1, 1993, Role of endorphins in benzodiazepine-induced hyperglycaemia in mice, Pharmacology Biochemistry and Behavior, 46(4):995-997.
Naltrexone (Oral Route), MayoClinic.com, 11 pp., 2009.
Nash et al., Jul. 1, 2004, Anxiety disorders, Medicine, 32(7):17-21.
National Institutes of Health, Apr. 18, 2008, Efficacy and safety study of combination therapy to treat uncomplicated obesity, http://clinicaltrials.gov/show/NCT00364871, 5 pp.
Navarro et al. (Jun. 2001) Topiramate for Clozapine-Induced Seizures, Am. J. Psychiatry, 158(6):968-969.
NDA 20-711, Approval Letter of Application No. NDA 20-711, Department of Health and Human Services, May 14, 1997, 4 pp.
NDA 20-789/S-005 Zonegran (zonisamide) Capsules 100 mg, FDA Approved Labeling Text dated Oct. 7, 2002, 2 pp.
NDA20-789, Zonegran (zonisamide) Capsules 100 mg, FDA Approved Labeling Text, p. 1-24 (Mar. 27, 2000).
Neumeister et al. 1999. Addition of naltrexone to fluoxetine in the treatment of binge eating disorder. Am. J. Psychiatry, 156(5):797.
NIH Publication No. 05-3892, Dec. 2004, National Diabetes Statistics, 18 pp.
Ninan et al., 1992, An improved synthesis of noroxymorphont, Tetrahedron., 48(32):6709-6716.
Nissen et al., 2016, Effect of naltrexone-bupropion on major adverse cardiovascular events in overweight and obese patients with cardiovascular risk factors, *Jama*, 315(10):990-1004.
Niswender et al. 1997. Effects of increased glucokinase gene copy number on glucose homeostatis and hepatic glucose metabolism. The Journal of Biological Chemistry, 272(36):22570-22575.
Note for guidance on stability testing of existing active substances and related finished product, Committee for Proprietary Medicinal Products (CPMP), Apr. 22, 1998, 9 pp.
Novi et al. (Apr.-Jun. 1990) The role of opioid antagonists in the treatment of obesity. Results of a clinical trial with naltrexone, Minerva Endocrinol. 15(2):121-123, Abstract.
O'Byrne et al., Jan. 1, 1990, Effects of drugs on glucose tolerance in non-insulin-dependent diabetes (part II), Drugs, Adis International Ltd., 40(2):204-219.
Okada et al. (1992) Effects of zonisamide on extracellular levels of monoamine and its metabolite, and on Ca2+ dependent dopamine release Epilepsy Research, 13:113-119.
Okada et al. (1995) Effects of zonisamide on dopaminergic system, Epilepsy Research, 22:198-205.
Olsen et al., (1990) Conjugate Addition Ligands of Opioid Antagonists. Methacrylate Esters and Ethers of 6Alpha- and 6Beta-Naltrexol, Journal of Medicinal Chemistry, American Chemical Society, 33(2):737-741.
Olszewski et al. (Jun. 13, 2001) Evidence of Interactions Between Melanocortin and Opioid Systems in Regulation of Feeding, NeuroReport, 12(8):1727-1730.
Oncken et al., 2001, Adverse effects of Oral naltrexone: an analysis of data from two clinical trials, Psychopharmacology, 154:397-402.
Oommen et al. (1999) Zonisamide: A new antiepileptic drug. Clinical Neuropharmacology, 22(4):192-200.
Orexigen Therapeutics Press Release: "Orexigen Therapeutics Provides Statement on Termination of the Light Study and Updates on Contrave Collaboration with Takeda Pharmaceuticals", May 12, 2015, retrieved from http://ir.orexigen.com/phoenix.zhtml?c=207034&p=irol-newsArticle_Print&ID-2047312.
Orexigen Therapeutics Press Release: "Takeda Pharmaceuticals and Orexigen Therapeutics Announce Termination of the Cardiovascular Outcomes Study (Light Study) of the Obesity Drug Contrave® (naltrexone HCI and bupropion HCI)", May 12, 2015, retrieved from http://ir.orexigen.com/phoenix.zhtml?c=207034&p=irol-newsArticle_Print&ID-2046959.
Orexigen Therapeutics, Inc., 2008, A safety and efficacy study comparing naltrexone SR/bupropion SR and placebo in obese type 2 diabetics, http://clinicaltrials.gov/ct2/show/NCT00474630, 3 pp.
Orexigen Therapeutics, Inc., Method-of-use study assessing the effect of naltrexone sustained release (SR)/bupropion SR on body weight and cardiovascular risk factors in overweight and obese subjects, http://clinicaltrials.gov/ct2/show/NCT01764386, 5 pp. Feb. 9, 2013.
Ortho-Novum Tablets and Modicon Tablets Prescribing Information, Apr. 2002, 8 pp.
Otake et al. (May 15, 2005) Association of visceral fat accumulation and plasma adiponectin and colorectal ademona: evidence for participation of insulin resistance, Clinical Cancer Research 11:3642-3646.
Ovadia, Oct. 1999, A Novel Twist on Binge Eating Treatment, Psychiatric Dispatches in Primary Psychiatry; 6(10):24-29.
Paar et al., 2002, Bivalent ligands with rigid double-stranded DNA spacers reveal structural constraints on signaling by FcεRI, J. Immunol., 169:856-864.
Padwal, Oct. 6, 2009, Contrave, a bupropion and naltrexone combination therapy for the potential treatment of obesity, Curr. Opin. Investig. Drugs, 10(10):1117-1125 (abstract).
Pagoto et al., Association of Major Depression and Binge Eating Disorder with Weight Loss in a Clinical Setting, Obesity, Nov. 2007; 15(11):2557-2559.
Paile-Hyvarinen et al., Mar. 14, 2003, Quality of life and metabolic status in mildly depressed women with type 2 diabetes treated with paroxetine: a single blind randomised placebo controlled trial, BMC Family Practice, Biomed Central, 4(1), 6 pp.
Pandit, 2007, Introduction to the Pharmaceutical Sciences, 1st Ed., Lippincott Williams & Wilkins, Baltimore, MD, p. 154.
Pasternak et al. (1980) Long-acting opiate agonists and antagonists: 14-hydroxydihydromorphinone hydrazones, Med. Chem, 23:674-676.
Patel et al., Jun. 2011, A hospital-based observational study of type 2 diabetic subjects from Gujarat, India, Journal of Health, Population and Nutrition, 29(3):265-272.
Pavuluri et al. (2002) Topiramate Plus Risperidone for Controlling Weight Gain and Symptoms in Preschool Mania, Journal of Child and Adolescent Psychopharmacology, 12(3):271-273.
Pearlstein et al., 2003, A double-blind, placebo-controlled trial of fluvoxamine in binge eating disorder; a high placebo response, Arch Womens Ment Health, 6:147-151.
Penn et al., 2003, Pharmacotherapy of obesity in the near term, Current Opinion in Endocrinology and Diabetes, 18(2):311-316.
Pfizer Inc., Apr. 2014, Embeda Prescription Information, 34 pp.
Plodkowski et al., 2009, Bupropion and naltrexone: a review of their use individually and in combination for the treatment of obesity, Expert Opin. Pharmacother. 10(6):1069-1081.
Portoghese et al., 1982, Opioid agonist and antagonist bivalent ligands as receptor probes, Life Sciences, 31:1283-1286.
Portoghese et al., 1986, Opioid agonist and antagonist bivalent ligands. The relationship between spacer length and selectivity at multiple opioid receptors, J. Med. Chem., 29:1855-1861.
Portoghese et al., 1986, Synthesis and Opioid antagonist potencies of naltrexamine bivalent ligands with conformationally restricted spacers J. Med. Chem., 29:1650-1653.
Portoghese, 1992, The role of concepts in structure-activity relationship studies of opioid ligands, J. Med. Chem., 35:1927-1937.
Potter et al., 1997, Sustained Weight Loss Associated with 12-month topiramate Therapy, Epilepsia, Raven Press Ltd. New York, 38(Suppl 8):97.
Ramlo-Halsted et al., 2000, The natural history of type 2 diabetes: practical points to consider in developing prevention and treatment strategies, Clin. Diabetes, 18(2).
Rao et al. (1998) Fixed-dose combination therapy: panacea or poison?, Intensive Care Med, 24:283-285.
Rao, Mar. 2001, Insulin resistance syndrome, American Family Physician, 63(6):1159-1163.
Reaven, G. M. 1995. Pathophysiology of insulin resistance in human disease. Physiological Reviews, 75(3):473-486.
Reents et al. (1988) Nalozone and naltrexone, Chest, 93(1):217-219.
Remington's Pharmaceutical Sciences, 1980, 16th ed., Mack Publishing Company, Arthur Osol. Editor, pp. 1553-1584.
Remington's Pharmaceutical Sciences, 1980, 16th ed., Mack Publishing Company, Arthur Osol. Editor, pp. 1592-1597, 1676-1678.
Remington's Pharmaceutical Sciences, 1980, 16th ed., Mack Publishing Company, Arthur Osol. Editor, pp. 1594-1613.

(56) References Cited

OTHER PUBLICATIONS

Remington's Pharmaceutical Sciences. 18th Edition; Easton, PA: Mack Publishing Co. (1990).
Reneric et al. (Nov. 1998) Opioid Receptor Antagonists in Psychiatry', CNS Drugs, 10(5):365-382.
Rezvani et al. 2000. Combination pharmacotherapy: A mixture of small doses of naltrexone, fluoxetine, and thyrotropin-releasing hormone analogue reduces alcohol intake in three strains of alcohol-preferring rats. Alcohol & Alcoholism, 35(1):76-83.
Ricca et al., 2001, Fluoxetine and fluvoxamine combined with individual cognitive-behavior therapy in binge-eating disorder: a one-year follow-up study, Psychotherapy and Psychosomatics, 70:298-306.
Richelsen et al., Feb. 1994, Growth hormone treatment of obese women for 5 wk: effect on body composition and adipose tissue LPL activity, Am J. Physiol., 266(2 Pt 1):11-16.
Romano et al. 2001. Long-term treatment of obsessive-compulsive disorder after an acute response: A comparison of fluoxetine versus placebo. Journal of Clinical Psychopharmacology, 21(1):46-52.
Rotzinger et al. (1999) Metabolism of some 'second' and 'fourth' generation antidepressants: iprindole, viloxazine, bupropion, mianserin, maprotiline, trazadone, nefazodone, and vaniafaxine, Cellular and Molecular Neurobiology, 19:430.
Rowland et al. (2001) Effects of the cannabinoid receptor antagonist SR 141716, alone and in combination with dexfenfluramine or naloxone, on food intake in rats. Psychopharmacology; 159:111-116.
Saba et al. 2002. Lamotrigine-clozapine combination in refractory schizophrenia: Three cases. The Journal of Neuropsychiatry and Clinical Neurosciences, 14(1):86.
Sackellares et al. (1985) Pilot study of zonisamide (1,2-benzisoxazole-3-methanesulfonamide) in patients with refractory partial seizures. Epilepsia, 26(3):206-211.
Saper et al. (2002) The need to feed: Homeostatic and hedonic control of eating, Neuron, 36:199-211.
Sashiwa et al., 2000, Chemical modification of chitosan. 3. Hyperbranched chitosan-sialic acid dendrimer hybrid with tetraethylene glycol spacer, Macromolecules, 33:6913-6915.
Sayre et al., 1984, Design and synthesis of naltrexone-derived affinity labels with nonequilibrium opioid agonist and antagonist activities. Evidence for the existence of different receptor subtypes in different tissues, J. Med. Chem., 27:1325-1335.
Scheen et al., May 1, 2005, Diabete sucre iatrogene: l'exemple des anti-phsychogiques atypiques, Revue Medicale de Liege, 60(5-6):455-460.
Schimmel et al., 1974, Inhibition by diphenylhydantoin of the diabetogenic action of streptozocin, Horm. Metab. Res. 6:475-477.
Schmidhammer et al. (1994) Mixed Azines of Naloxone with Dihydromorphinone Derivatives. A. Helv. Chim. Acta; 77:999-1002.
Schmidt et al. (1993) Zonisamide for add-on treatment of refractory partial epilepsy: a European double-blind trial. Epilepsy Research; 15:67-73.
Schneider et al., Sep. 15, 2009, Design and methods for a randomized clinical trial treating comorbid obesity and major depressive disorder, BMC Psychiatry, 8:77.
Shapira et al. (2000) Treatment of Binge-Eating Disorder with Topiramate: A Clinical Case Series. J. Clin. Psychiatry; 61(5):368-371.
Shapira et al. 2004. A double-blind, placebo-controlled trial of olanzapine addition in fluoxetine-refractory obsessive-compulsive disorder. Biol. Psychiatry, 550:553-555.
Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.
Shelton (2003) Classification of Antidepressants and their Clinical Implications, Primary Care Companion J. Clin. Psychiatry, 5(Supp. 7):27-32.
Shriqui et al. (Jul. 2002) Atypical Antipsychotics, The Canadian Journal of CME, pp. 65-80.
Shuman et al., Jun. 1986, Abnormal body fat distribution detected by computed tomography in diabetic men, Investigative Radiology, 21(6):483-487.
Sitsen et al., 2001, Drug-drug interaction studies with mirtazapine and carbamazepine in healthy male subjects, European Journal of Drug Metabolism and Pharmacokinetics, 26(1-2):109-121.
Sleep Disorders, in Diagnostic and Statistical Manual of Mental Disorders, 4th Edition, American Psychiatric Association, p. 583-595 (2000).
Sneer et al., Protective effect of diphenylhydantoin on the diabetes-inducing effect of alioxan, database accession No. 1980:34024.
Spiegel et al., 1987, Effect of naltrexone on food intake, hunger, and satiety in obese men, Physiology & Behavior, 40(2):135-141.
Spigset et al. (2001) Therapeutic Approaches to Bulimia Nervosa, Expert Opinion on Therapeutic Patents, 11(3):463-477.
Srivastava et al. 1975. Organic disulfides and related substances. 38. Some disulfide and trisulfide sulfinate salts as antiradiation drugs. Journal of Medicinal Chemistry, 18(8):798-802.
Stansfeld et al., Aug. 1992, Social class and minor psychiatric disorder in British civil servants: a validated screening survey using the General Health Questionnaire, Psychological Medicine, 22:739-749.
Stedman's Medical Dictionary, 28th ed., Lippincott Williams & Wilkins, Philadelphia, 1999, pp. 490-491 and 1552.
Steffen et al. 2006. Emerging drugs for eating disorder treatment. Expert Opin. Emerging Drugs, 11(2):315-336.
Stein (Feb. 15, 2000) Neurobiology of the obsessive-compulsive spectrum disorders, Biological Psychiatry 47(4):296-304.
Stein (Aug. 3, 2002) Obsessive-compulsive disorder, Lancet 360(9330):397-405.
Stepinski et al., 1991, Use of hydrophilic diamines for bridging of two opioid peptide pharmacophores, Internat. J. of Peptide & Protein Res., 38:588-592.
Storch et al. 2006. Clinical predictors of early fluoxetine treatment response in obsessive-compulsive disorder. Depression and Anxiety, 23:429-433.
Stromberg et al. (2002) A comparison of the effects of 6-beta naltrexol and naltrexone on the consumption of ethanol or sucrose using a limited-access procedure in rats. Pharmacology, Biochemistry, and Behavior, 72:483-490.
Swedo et al. 1998. Pediatric autoimmune neuropsychiatric disorders associated with streptococcal infections: Clinical description of the first 50 cases. Am. J. Psychiatry, 155(2):264-271.
Symons et al. 2004. Self-injurious behavior and the efficacy of naltrexone treatment: A quantitative synthesis. Mental Retardation and Developmental Disabilities Research Reviews, 10:193-200.
Tallarida et al., 1996, Testing for synergism over a range of fixed ratio drug combinations: replacing the isobologram, Life Sciences, 58(2):PL23-PL28.
Tallarida, 2001, Drug synergism: its detection and applications, J. Pharmacol. and Expt. Therap., 298(3):865-872.
Tamiz et al., 2000, Application of the bivalent ligand approach to the design of novel dimeric serotonin reuptake inhibitors, J. Am. Chem. Soc., 122:5393-5394.
Tamiz et al., 2001, Pharmacological and behavioral analysis of the effects of some bivalent ligand-based monoamine reuptake inhibitors, J. Med. Chem., 44:1615-1622.
Tavakoli et al., Jul. 2003, Diabetic ketoacidosis in a patient with olanzapine, valproic acid, and venlafaxine, Southern Medical Journal, 96(7):729-730.
Testa, 2004, Prodrug research: futile or fertile?, Biochemical Pharmacology, 68:2097-2106.
Thearle et al. (2003) Obesity and Pharmacology, Endocrinology and Metabolism Clinics of North American, W.B. Suanders Company, Philadelphia US 32(4):1005-1024.
Thombre et al. (2004) Osmotic drug delivery using swellable-core technology, Journal of Controlled Release 94:75-89.
Tollefson et al. (1997) Olanzapine versus haloperidol in the treatment of schizophrenia and schizoaffective and schizophreniform disorders: results of an international collaborative trial, Am J. Psychiatry, 154(5):457-465.

(56) References Cited

OTHER PUBLICATIONS

Trexan® (naltrexone hydrochloride), in Physicians' Desk Reference, 49th edition, 1995, pp. 965-967.
Turnbull et al., Jan. 1985, The effect of valproate on blood metabolite concentrations in spontaneously diabetic, ketoacidotic, bb/e wistar rats, Diabetes Research 2(1):45-48.
Tutka et al., 2004, Convulsant and anticonvulsant effects of bupropion in mice, European Journal of Pharmacology, 499:117-120.
Van Gaal et al., Aug. 1998, Sibutramine and fat distribution: is there a role for pharmacotherapy in abdominal/visceral fat reduction?, Int J Obes Relat Metab Disord, Suppl 1:S38-40; discussion S41-2.
Van Schaftingen et al. (1992) The regulatory protein of liver glucokinase. Advan. Enzyme Regul., 32:133-148.
Verebey, 1981, Quantitative determination of naltrexone, 6 β-naltrexol and 2-hydroxy-3-methoxy-6 β-naltrexol (HMN) in human plasma, red blood cells, saliva and urine by gas liquid chromatography, National Institute on Drug Abuse Research Monograph Series 28:36-51.
Verebey, 1981, The clinical pharmacology of naltrexone: pharmacology and pharmacodynamics, National Institute on Drug Abuse Research Monograph Series 28:147-158.
Vieta et al. (2003) 1-year follow-up of patients treated with risperidone and topiramate for a manic episode, J Clin Psychiatry, 64(7):834-829.
Vieta et al. (2004) Effects on weight and outcome of long-term olanzapine-topiramate combination treatment in bipolar disorder. Journal of Clinical Psychopharmacology 24(4):374-378.
Vythilingum et al. 2005. Obsessive-compulsive disorders and dermatologic disease. Dermatologic Clinics, 23:675-680.
Wadden et al. (2000) Effects of Sibutramine Plus Orlistat in Obese Women Following 1 Year of Treatment by Sibutramine Alone: A Placebo-Controlled Trial, Obesity Research; 8(6):431.
Wadden et al., Jan. 2011, Weight loss with naltrexone SR/bupropion SR combination therapy as an adjunct to behavior modification: the COR-BMOD trial, Obesity, 19(1):110-120.
Walker et al. (1988) Chronic Toxicity of the Anticonvulsant Zonisamide in Beagle Dogs, Fundamental and Applied Toxicology 11:333-342.
Wall et al., Jul./Aug. 1981, Metabolism and disposition of naltrexone in man after oral and intravenous administration, Drug Metabolism and Disposition, 9(4):369-375.
Wang et al. (2002) Gabapentin augmentation therapy in bipolar depression, Bipolar Disorders 4:296-301.
Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.
Wellbutrin® (bupropion hydrochloride) tablets, in Physicians Desk Reference, 49th edition, 1995, pp. 824-827, 150.
Welty et al. (Nov. 30-Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.
Wermuth, Apr. 2006, Similarity in drugs: reflections on analogue design, Drug Discovery Today, 11(7/8):348-354.
Werneke et al. (2002) Options for Pharmacological Management of Obesity in patients Treated with Atypical Antipsychotics, International Clinical Psychopharmacology, 17(4):145-160.
Wheatley et al., 1998, Mirtazapine: efficacy and tolerability in comparison with fluoxetine in patients with moderate to severe major depressive disorder, J. Clin Psychiatry, 59(6):306-312, Abstract.
White et al. 2002. Development and validation of the food-craving inventory. Obesity Research, 10(2):107-114.
White et al., 2003, Clarifying the role of insulin in type 2 diabetes management, Clinical Diabetes, 21(1):14-21.
Wieczorek et al., 2001, The effects of the selective serotonin reuptake-inhibitor fluvoxamine on body weight in Zucker rats are mediated by cortocotrophin-releasing hormone, International Journal of Obesity, 25(10):1566-1569.
Wilcox et al., 2009, An open-label study of naltrexone and bupropion combination therapy for smoking cessation in overweight and obese subjects, Addictive Behaviors, 35(3):229-234.
Wilding (2004) Clinical evaluation of anti-obesity drugs. Current Drug Targets; 5:325-332.
Willmore, L. J. 2004. Commentary on Leppik. Seizure, 13S:S10.
Wilner, 2002, Is Weight Loss With Zonisamide Gender-Specific?, Annual Meeting of the American Epilepsy Society, https://secure.neurohub.net/cgi-perl/get.cgi?pub=52318&ext-htm, 1 pp.
Winstanley et al., 1989, The effects of food on drug bioavailability, Br. J. clin. Pharmac. 28:621-628.
Wolff (1995) Burger's Medicinal Chemistry and Drug Discovery, John Wiley & Sons, 5th Ed. 1:975-977.
Wong et al., Aug. 2004, Starting insulin treatment in type 2 diabetes, Australian Prescriber, 27(4):93-96.
Yeomans et al. (2002) Opioid peptides and the control of human ingestive behaviour, Neuroscience and Biobehavioral Reviews, 26:712-728.
Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).
Yu et al. (2005) Influence of insulin treatment on insulin sensitivity in insulin requiring type 2 diabetes patents, Diabetes Research and Clinical Practice, 6881:854-859.
Zeng et al., 1988, Convenient synthesis of 9-alkyl and 9-arylacridines from [2-(trimethylsilypethoxy]methyl (sem) protected acridone, Tetrahedron Letters, 29(40):5123-5124.
Zhang et al. (1994) Positional Cloning of the Mouse obese gen and its humane homologue, Nature, 372:425-432.
Zhu et al. (Apr. 3, 2002) Pharmacologic Treatment of Eating Disorders, Canadian Journal of Psychiatry, 47(3):227-234.
Zitterl et al. 1999. Efficacy of fluoxetine in Austrian patients with obsessive-compulsive disorder. Wiener Klinische Wochenschrift, 111(11):439-442.
Zohar et al. 1987. Serotonergic responsivity in obsessive-compulsive disorder. Arch. Gen. Psychiatry, 44:946-951.
Zonisamide (Oral Route), MayoClinic.com, 12 pp., 2009.
ISR and WO dated May 11, 2012 in PCT/US11/63177.
International Search Report and Written Opinion dated Oct. 29, 2013 in PCT/US13/44368.
Anonymous, Jun. 7, 2008, Orexigen® Therapeutics announces that Contrave® may reverse the incidence of metabolic syndrome, PipelinReview.com.
Anonymous, Nov. 24, 2013, Positive interim analysis of the light study, testing weight loss medication, Physicans' Academy for Cardiovascular Education-News, Orexigen press release.
Chilton et al., Oct. 2, 2011, Neltraxone SR/Bupropion SR combination therapy improves predicted 10-year risk of cardiovascular disease, coronary heart disease, myocardial infarcation, and congestive heart failure, Obesity, 19(Suppl 1):S177.
Cleary et al., Jul. 1996, Naloxone effect on sucrose-motivated behavior, Psychopharmacology (Berl.), 126(2):110-114.
ClinicalTrials.gov, Dec. 20, 2006, Placebo-controlled trial of bupropion for the treatment of binge eating disorder, https://clinicaltrials.gov/ct2/show/study/NCT00414167, 3 pp.
Contrave (naltrexone HCI and bupropion HCI) extended-release tablets, initial U.S. approval, 2014.
Cusin et al., 2009, Chapter 2: Rating scales for depression, Handbook of Clinical Rating Scales and Assessment in Psychiatry and Mental Health, Baer et al., eds., Humana Press, pp. 7-35.
Fava, 2005, 15 years of clinical experience with bupropion HCI: from bupropion to bupropion SR to bupropion XL, Prim, Care Companion J. Clin Psychiatry, 7:106-113.
Miller et al., May 2006, Metabolic syndrome: screening, diagnosis, and management, Journal of Midwifery & Women's Health, 51(3):141-151.
Minnaro et al., 1997, Aspectos technologicos de las formas farmaceuticas de liberacion modificada de administracion oral: sistemas matriciales, flotantes y bioadhesivos, Cienc. Pharm, 7(3):113-121.
NIH News Release, First federal obesity clinical guidelines released, Jun. 17, 1998, 3 pp.

(56) References Cited

OTHER PUBLICATIONS

O'Neil et al., Oct. 3, 2011, Naltrexone SR/Bupropion SR and intensive behavioral modification combination increases the likelihood of achieving early and sustained weight loss and associated improvement in markers of cardiometabolic risk, Obesity, 19(Suppl 1):S179-S180.

Orexigen Therapeutics Press Release, Feb. 1, 2011, FDA issues complete response to new drug application for Contrave ® for the management of obesity, 3 pp.

Padwal et al., Oct. 2009, Contrave, a bupropion and naltrexone combination therapy for the potential treatment of obesity, Current Opinion in Investigational Drugs, 10:1117-1125.

Remington: The Science and Practice of Pharmacy, 20th Ed., Chapter 45: Oral Solid Dosage Forms, pp. 858-893, 2003.

Shikh, Jan. 27, 2007, Bioavailablity of oral medications, Russian Medical Journal, 2:95.

Sneer et al., 1979, Revista medico-chirurgicala, 83(1):87-91.

Thorndike, Jan. 28, 2008, Depressive symptoms and smoking cessation after hospitalization for cardiovascular disease, Arch Intern Med, 168(2):186-191.

White et al., 2013, Buproprion for overweight women with binge-eating disorder: a randomized, double-blind, placebo-controlled trial, J. Clin. Psychiatry, 74(4):400-406.

Wikipedia, Major depressive disorder, downloaded on Oct. 9, 2017 from en.wikipedia.org.wiki/Major_depressive_disorder, 1 p.

www.1000mealplans.com (accessed Feb. 21, 2017), 2 pp.

* cited by examiner

METHODS OF TREATING OVERWEIGHT AND OBESITY

RELATED APPLICATIONS

The present application is a continuation of U.S. application Ser. No. 14/405,775, which is the U.S. National Phase under 35 U.S.C. § 371 of International Application No. PCT/US2013/044368, entitled "METHODS OF TREATING OVERWEIGHT AND OBESITY," filed Jun. 5, 2013, and published in English on Dec. 12, 2013 as WO 2013/184837, which is a non-provisional of and claims priority to U.S. Provisional Application No. 61/656,451 filed on Jun. 6, 2012, which, where permitted, is herein incorporated by reference in its entirety.

BACKGROUND

Field of the Invention

The present disclosure relates to compositions, kits, uses, systems and methods for treating overweight and obesity using naltrexone plus bupropion, preferably in combination with a comprehensive web-based and/or telephone-based weight management program, and optionally in subjects at increased risk of adverse cardiovascular outcomes.

Description of the Related Art

Obesity has been defined in terms of body mass index (BMI). BMI is calculated as weight (kg)/[height (m)]$^2$. According to the guidelines of the U.S. Centers for Disease Control and Prevention (CDC) and the World Health Organization (WHO), for adults over 20 years old, BMI is categorized as follows: below 18.5 is considered underweight, 18.5-24.9 is considered normal, 25.0-29.9 is considered overweight, and 30.0 and above is considered obese (World Health Organization. Physical status: The use and interpretation of anthropometry. Geneva, Switzerland: World Health Organization 1995. WHO Technical Report Series).

The prevalence of obesity has markedly increased over the past three decades, with 32% of men and 36% of women considered obese. These individuals are at increased risk for a variety of chronic conditions associated with obesity, including type 2 diabetes, coronary heart disease, hypertension, stroke, dyslipidemia, gallbladder disease, sleep apnea, certain types of cancer, and osteoarthritis, as well as increased mortality risk from all causes (NHLBI Clinical Guidelines, 1998). Overweight and obesity are also associated with increased all-cause mortality.

Diet and exercise-based behavioral modification is the mainstay of weight management therapy. However, such intervention is often of limited effectiveness and difficult for individuals to adhere to. Therefore, pharmacotherapy has been employed as an adjunct to diet and exercise. Orlistat, lorcaserin, and phentermine/topiramate are currently the only three drugs approved in the United States for the long-term treatment of obesity. A 5-10% weight loss has been determined to lead to significant medical benefits. While orlistat has a favorable safety profile, it can cause loose stools and fecal incontinence, making acceptance by patients difficult. Bariatric surgery (specifically gastric banding) is now indicated for subjects with BMI≥30 kg/m2 who have at least one obesity-related comorbidity. While effective in most cases, it is invasive with possible complications including infection, death, hypoglycemia, failure to lose weight, gastrointestinal symptoms, nutritional deficiencies, depression, sexual and relationship problems, and noncompliance with behavioral recommendations.

U.S. Pat. Nos. 7,375,111 and 7,462,626 disclose the combination of naltrexone and bupropion (NB) for weight loss therapy. Wadden et al. disclose the combination of naltrexone and bupropion as an adjunct to an intensive behavioral modification (BMOD) program for weight loss. *Obesity* (2011) 19:110-120. The BMOD program described by Wadden et al. was delivered in person to groups of 10-20 persons. Group meetings lasted 90 min and were held weekly for the first 16 weeks, every other week for the next 12 weeks, and monthly thereafter (yielding a total of 28 sessions). Group sessions typically began with a review of participants' eating and activity records and other homework assignments. Group leaders then introduced a new topic in weight control which, during the first 16 weeks, included meal planning, stimulus control, slowing eating, problem solving, social support, and coping with high risk situations. Subsequent sessions covered skills required for maintaining lost weight.

While the combination of naltrexone and bupropion is known to be efficacious for weight management for some patient populations, alone or in combination with an intensive BMOD program, a need exists for an effective treatment of overweight or obesity in subjects at increased risk of adverse cardiovascular outcomes. In addition, there exists a need for a weight management program for use in combination with naltrexone and bupropion that is easier for patients to comply with than existing BMOD programs, but which is still efficacious, particularly in subjects at increased risk of adverse cardiovascular outcomes.

SUMMARY

An embodiment of the invention includes a method of treating a subject at increased risk of an adverse cardiovascular outcome comprising for overweight or obesity: identifying an overweight or obese subject at increased risk of an adverse cardiovascular outcome; and administering to the subject a therapeutically effective amount of sustained release naltrexone, or a pharmaceutically acceptable salt thereof, and sustained release bupropion, or a pharmaceutically acceptable salt thereof. In some embodiments, aid overweight or obese subject is identified as being at increased risk of an adverse cardiovascular outcome if the subject: a.) is diagnosed as having cardiovascular disease with at least one risk factor selected from the group consisting of: a history of documented myocardial infarction >3 months prior to the identification; a history of coronary revascularization including coronary artery bypass graft surgery, stent placement, percutaneous transluminal coronary angioplasty, or laser atherectomy; a history of carotid or peripheral revascularization, including carotid endarterectomy, lower extremity atherosclerotic disease atherectomy, repair of abdominal aorta aneurysm, femoral or popliteal bypass; angina with ischemic changes, ECG changes on a graded exercise test, or positive cardiac imaging study; ankle brachial index <0.9 assessed by simple palpation within prior 2 years of the identification; and ≥50% stenosis of a coronary, carotid, or lower extremity artery within prior 2 years of the identification; and/or b.) is diagnosed as having Type 2 diabetes mellitus with at least 2 risk factors selected from the group consisting of: hypertension controlled with or without pharmacotherapy at <145/95 mm Hg; dyslipidemia requiring pharmacotherapy; documented low HDL cholesterol, <50 mg/dL in women or <40 mg/dL in men, within prior 12 months of the identification; and current tobacco smoker.

In some embodiments, the method further comprises a lead-in 2-week period during which the subject receive treatment according to one of two sequences: 1 week of active study medication comprising sustained release naltrexone, or a pharmaceutically acceptable salt thereof, and sustained release bupropion, or a pharmaceutically acceptable salt thereof, once a day followed by 1 week of placebo once a day; or 1 week of placebo followed by 1 week of active study medication comprising sustained release naltrexone, or a pharmaceutically acceptable salt thereof, and sustained release bupropion, or a pharmaceutically acceptable salt thereof.

In some embodiments, the subject does not have one or more characteristics selected from the group consisting of: myocardial infarction within 3 months prior to the identification; angina pectoris Grade III or IV as per the Canadian Cardiovascular Society grading scheme; a clinical history of cerebrovascular disease including stroke; a history of tachyarrhythmia other than sinus tachycardia; blood pressure ≥145/95 mm Hg, irrespective of treatment with antihypertensive agents; unstable weight within 3 months prior to the identification; planned bariatric surgery, cardiac surgery, or coronary angioplasty; severe renal impairment defined by an estimated GFR <30 mL/min; clinical history of liver failure or documented ALT or AST greater than 3 times the upper limit of normal; known infection with HIV or hepatitis; chronic use or positive screen for opioids; recent drug or alcohol abuse or dependence, with the exception of nicotine dependence, within 6 months prior to the identification; history of seizures, including febrile seizures, cranial trauma, or other conditions that predispose the subject to seizures; history of mania or current diagnosis of active psychosis, active bulimia or anorexia nervosa, but not binge eating disorder; a risk for suicide attempts; acute depressive illness including new onset of depression or acute exacerbation of symptoms, but not stable subjects on chronic treatment for depression; any condition with life expectancy anticipated to be less than 4 years including congestive heart failure NYHA Class 3 or 4; a history of malignancy within the previous 5 years, not including non-melanoma skin cancer or surgically cured cervical cancer; current use of other bupropion or naltrexone containing products; a history of hypersensitivity or intolerance to naltrexone or bupropion; use of monoamine oxidase inhibitors within 14 days prior to the identification; use of any investigational drug, device, or procedure within 30 days prior to the identification; a pregnant or breast-feeding woman, or currently trying to become pregnant, or of child-bearing potential, including pen-menopausal women who have had a menstrual period within one year, and not willing to practice birth control; and inability to consistently access broadband internet.

In some embodiments, the method further comprises providing the subject with a web-based weight management program, a phone-based weight management program, or a combination thereof.

An embodiment of the invention includes a method of treating a subject for overweight or obesity comprising: identifying an overweight or obese subject; and administering to the subject a therapeutically effective amount of sustained release naltrexone, or a pharmaceutically acceptable salt thereof, and sustained release bupropion, or a pharmaceutically acceptable salt thereof, in combination with a web-based weight management program, a phone-based weight management program, or a combination thereof.

In some embodiments, the identified subject has a BMI≥30 and ≥45 kg/m2 with uncomplicated obesity. In some embodiments, the identified subject has a BMI of ≥27 and ≤45 kg/m2 with dyslipidemia and/or controlled hypertension. In some embodiments, the subject is treated for at least 26 weeks. In some embodiments, the phone-based weight management program comprise one or more coaching calls to the subject. In some embodiments, the phone-based weight management program optionally comprises one or more web coaching tools. In some embodiments, the web-based or phone-based weight management program provides the subject with one or more of behavioral, nutritional or fitness education.

In some embodiments, the education are delivered by a trained health or fitness coach and/or a registered dietitian. In some embodiments, the trained health or fitness coach and/or the registered dietitian counsel the subject via the phone or via a website for the subject, and provide one or more of the topics selected from the group consisting of tips and motivational messages; coaching through question and answer; weekly office hours for real-time responses to the subject's inquiries via the website; weekly educational materials; video lessons; weight, exercise, or diet tracking with badge rewards; goal setting; progress tracking; and communications to encourage the subject to engage in the weight management program.

In some embodiments, 32 mg per day of sustained release naltrexone, or a pharmaceutically acceptable salt thereof, and 360 mg per day of sustained release bupropion, or a pharmaceutically acceptable salt thereof, is administered to the subject. In some embodiments, the subject is administered the sustained release naltrexone, or a pharmaceutically acceptable salt thereof, and the sustained release bupropion, or a pharmaceutically acceptable salt thereof, in a tablet containing 8 mg of sustained release naltrexone and 90 mg of sustained release bupropion.

In some embodiments, the treatment with naltrexone and bupropion does not increase the subject's risk of an adverse cardiovascular outcome. In some embodiments, the treatment with naltrexone and bupropion decreases the subject's risk of an adverse cardiovascular outcome. In some embodiments, the adverse cardiovascular outcome is cardiovascular death, nonfatal myocardial infarction, or nonfatal stroke. In some embodiments, the subject achieves a percentage of weight loss of at least 5%, at least 10% or at least 15%. In some embodiments, the weight management program has a period of at least 52 weeks or at least 78 weeks.

In some embodiments, the subject does not receive in-person counseling as part of a weight management program. In some embodiments, the subject does not receive more than 5 in-person counseling sessions as part of a weight management program. In some embodiments, the subject does not receive an intensive behavioral modification (BMOD) program for weight loss.

BRIEF DESCRIPTION OF THE DRAWINGS

So that the manner in which the recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

DETAILED DESCRIPTION

Figure 1:
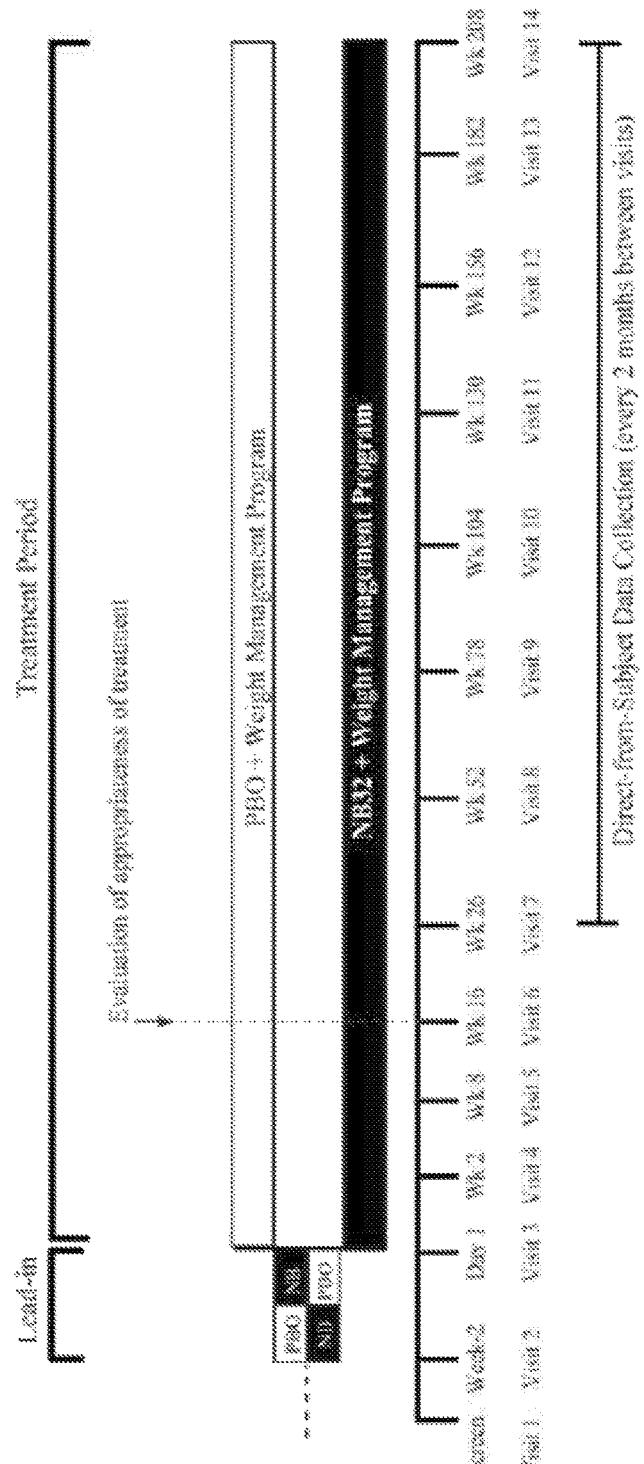
FIG. 1 shows a visual representation of a study design demonstrating that treatment with Naltrexone SR/Bupropion SR does not increase or decreases the occurrence of Major Adverse Cardiovascular Events (MACE) in overweight and obese subjects with cardiovascular risk factors as presented in Example 1.
Figure 2:
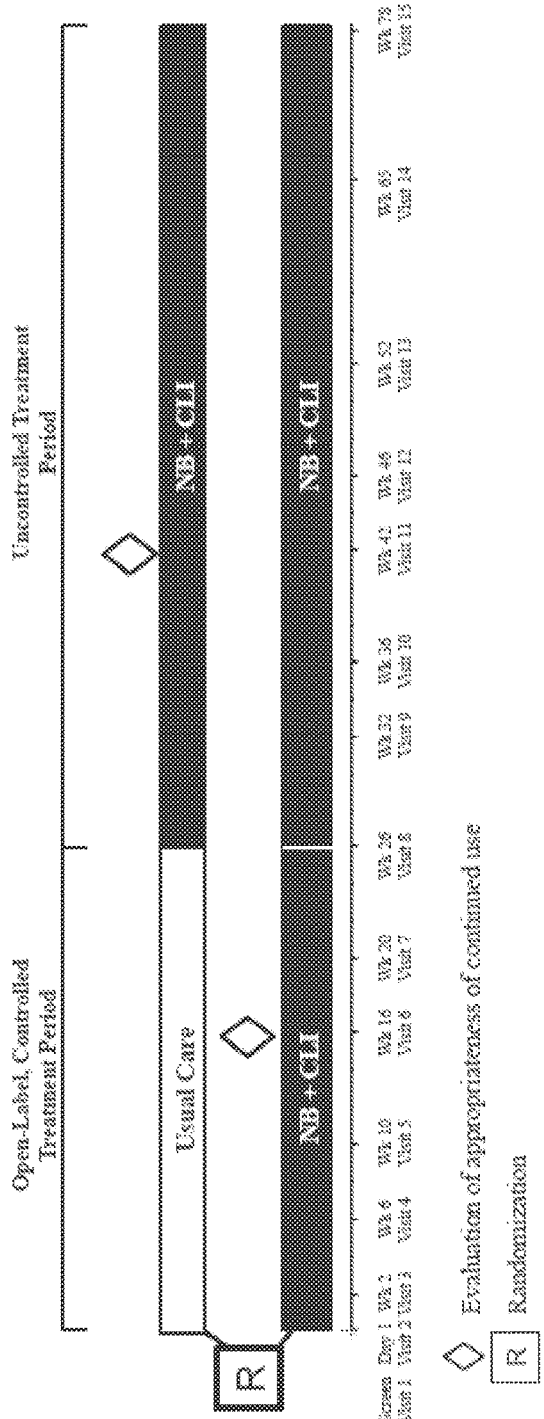
FIG. 2 shows a visual representation of a study design demonstrating the beneficial effect of Naltrexone SR/Bupropion SR on body weight and cardiovascular risk factors in overweight and obese subjects in conjunction with a comprehensive lifestyle intervention (CLI) program compared minimal lifestyle intervention program as presented in Example 2.

The present disclosure relates to compositions, kits, uses, systems and methods for treating overweight and obesity using naltrexone plus bupropion, preferably in combination with a comprehensive lifestyle intervention (CLI) program including a web-based weight management program, a phone-based weight management program, and a combination thereof. In some embodiments, the subject being treated for overweight and obesity are subjects at increased risk of adverse cardiovascular outcomes. In a preferred embodiment, the treatment of a subject at increased risk of adverse cardiovascular outcomes with naltrexone plus bupropion in combination with a comprehensive web-based and/or telephone-based weight management program results in no more major adverse cardiovascular outcomes than treatment with the web-based and/or telephone-based weight management program alone. In some embodiments, the treatment of a subject at increased risk of adverse cardiovascular outcomes with naltrexone plus bupropion in combination with a comprehensive web-based and/or telephone-based weight management program surprisingly results in fewer major adverse cardiovascular outcomes than treatment with the web-based and/or telephone-based weight management program alone. Major adverse cardiovascular outcomes are cardiovascular death (including fatal myocardial infarction and fatal stroke), nonfatal myocardial infarction, nonfatal stroke, or nonfatal unstable angina requiring hospitalization.

In some embodiments, the subject being treated by the methods disclosed herein is at increased risk of adverse cardiovascular outcomes. Subjects at increased risk of adverse cardiovascular outcomes include subjects having a.) cardiovascular disease (confirmed diagnosis or at high likelihood of cardiovascular disease) with at least one of the following: history of documented myocardial infarction >3 months prior to screening; history of coronary revascularization (i.e., coronary artery bypass graft surgery, stent placement, percutaneous transluminal coronary angioplasty, or laser atherectomy); history of carotid or peripheral revascularization (i.e., carotid endarterectomy, lower extremity atherosclerotic disease atherectomy, repair of abdominal aorta aneurysm, femoral or popliteal bypass); angina with ischemic changes (resting ECG), ECG changes on a graded exercise test (GXT), or positive cardiac imaging study; ankle brachial index <0.9 (by simple palpation) within prior 2 years; ≥50% stenosis of a coronary, carotid, or lower extremity artery within prior 2 years; and/or b. Type 2 diabetes mellitus with at least 2 of the following: hypertension (controlled with or without pharmacotherapy at <145/95 mm Hg); dyslipidemia requiring pharmacotherapy; documented low HDL cholesterol (<50 mg/dL in women or <40 mg/dL in men) within prior 12 months; current tobacco smoker.

In some such embodiments, the subject being treated has uncomplicated obesity. In some other embodiments, the subject being treated is overweight and has dyslipidemia and/or controlled hypertension. In some embodiments, the subject being treated by the methods disclosed herein is not at increased risk of adverse cardiovascular outcomes.

In some embodiments the treatment with naltrexone and bupropion is combined with a weight management program. In some embodiments, the weight management program is a web-based program. In some other embodiments, the weight management program is a phone-based program. In some other embodiments, the weight management program is a combination of both web-based and phone based programs. In some embodiments, the subject does not receive more than 15, 10, 5, 4, 3, 2, or 1 in-person counseling sessions as part of a weight management program. In some embodiments, the subject does not receive any in-person counseling sessions as part of a weight management program.

Web-Based Weight Management Program

Preferably, the web-based program provides a progressive nutrition and exercise program with goal setting and tracking tools. Each subject is assigned to a health and fitness professional who counsels them online throughout the program. Additional educational tools include weekly web-based informational, educational and motivational resources supplemented by video lessons (Table 1) presented at regular intervals. Content for the program consists of: a weekly email that announces the goals for the week, provides motivation, and encourages continued participation; weekly goals (from email) that align with each week's theme (Table 1), along with a detailed explanation and a strategy for achieving these goals, placed on the MyWeightMate.com subject pages; three pieces of additional weekly content posted to user pages (tips and educational information) to help subjects reach their weekly goals; motivational messages throughout the week posted on participant pages; triggered event emails sent to users based on behaviors (i.e. absence from program activity, successful logging); video lessons provided on the MyWeightMate.com site for participants to view and archived for future access: weekly for the first 16 weeks, biweekly for the next 12 weeks, monthly for the remaining duration of the study, and two refresher campaigns that include 4 weekly sessions each year during the third and fourth year of the trial. Video lessons focus on relevant topics and are developed by subject matter experts.

TABLE 1

Weekly Themes and Video Topics for First 16 Weeks of the Weight Management Program

| Week | Theme | Video Lesson Topic |
|---|---|---|
| 1 | Get Started | Setting Yourself Up For Success: Getting Your Mind Right |
| 2 | Perfect Portions | SMART Goals |
| 3 | Avoid Pitfalls | Proper Form When You Move |
| 4 | Get More Vitamin Zzz | Healthful Substitutions for Food and Exercise |
| 5 | Boost Your Fitness | Fitness Myths |
| 6 | Skinny Food Secrets | Smart Strategies for Eating Less |
| 7 | Smash Sugar Spikes | How Do You Make Time For Your Health and Why is It Psychologically Important? |
| 8 | Take the Show on the Road | Accidental Exercise |
| 9 | Take Some Pressure Off | Powering Up Your Exercise |
| 10 | Metabolism Superchargers | Staying Fit If You Sit |
| 11 | Clobber High Cholesterol | Healthy Choices |
| 12 | Motivation Boosters | Breaking Weight Loss Plateaus |
| 13 | Kick It Up | Replacing Bad Habits With Healthy Ones |

TABLE 1-continued

Weekly Themes and Video Topics for First 16 Weeks of the Weight Management Program

| Week | Theme | Video Lesson Topic |
|------|-------|--------------------|
| 14 | Rut Busters | The Diet Hype Trap |
| 15 | Shore Up Your Self-Confidence | Healthy Living Guide: Live Your Best Life |
| 16 | Review and Renew | Boost Your Metabolism |

The web-based weight management program provides behavioral, nutritional and fitness education delivered by trained health and fitness coaches. The website provides a "WeightMate Coach" who counsels the subject via the participant's individual webpage, and provides one or more of the following: tips and motivational messages; coaching through Q&A; weekly office hours for real-time response via the website; weekly educational materials; content developed with subject matter experts; video lessons to supplement the weekly themes; weight, exercise, and diet tracking with badge rewards; suggested activity and coaching tip; communication to encourage engagement; and a contemporary website that is fun and intuitive.

In one embodiment, new themes and goals are introduced each Monday, with 2-3 goals of the week, relevant content and/or video lesson(s) (Table 1) are provided, and motivational messages are provided on one or more days of the week. Optionally, additional tips are provided one or more days during the week. In some embodiments, video lessons supplement the weekly educational themes. The produced video content ensures quality and uniformity of message to subjects, and a Q&A function allows patients to ask questions with <24 hour turnaround.

In some embodiments, web-based individual counseling is provided by a coach; preferably the subject has unlimited access to coach. Preferably the coach provides a schedule to the subject which includes weekly 'office hours' for real-time Q&A responses. The program emphasizes weekly weigh ins with daily food and activity tracking. Preferably, the website can track calories for each meal using a computer database of calories for specific foods and/or meals, and save favorite foods and meals. Four reference menus based on caloric needs and food preferences are provided. In some embodiments the subject is rewarded with badges for meeting particular goals (e.g., for 7 days of activity logged; for 7 days of food logged; for 3 weeks of weight logged; for first 15 pounds lost; for 12 weeks of program participation; for 26 weeks of program participation; for 52 weeks of program participation; for 78 weeks of program participation; for 5% weight loss; for 10% weight loss; for 15% weight loss). In a preferred embodiment, the subject periodically establishes a weight loss goal which is recorded as part of the program. The subject's progress toward the subject's goal(s) can be provided to the subject via the subject's webpage. The weight loss goal can be the goal for a one week, two week, month, two month, six month, year or longer period of time. The program provides the option for the participating subject to set a specific weight loss goal at the beginning of the program. The program also provides the option to track and log weight loss, and the progress towards achieving the specific goal on a daily or weekly basis. Optionally, a graphic representation of weight loss progress is provided to the subject via the subject's webpage. Periodic encouraging messages (e.g., badges and award notes) can be provided. Preferably, behavior-based automated messages from trainers are provided for increased motivation and participation.

In some embodiments, the exercise portion of the web-based weight management program encourages 5 days of activity and 2 days of rest, preferably on non-consecutive days (e.g. Monday and Friday). In some embodiments, the exercise program provides instructions on stretching, walking and other light cardio activity. Video clips can provide educational demonstration for stretches and exercise maneuvers. The website can track calories burned by the subject through exercise and activity logs.

In a preferred embodiment, the web-based weight management program does not involve any in-person therapy or group meetings.

Phone-Based Weight Management Program

In some embodiments, the telephone-based program comprises personalized coaching through one or more phone calls. In one embodiment, the phone calls are conducted by a dedicated coach to the subject receiving treatment. In another embodiment, the phone calls are conducted by a registered dietitian to the subject receiving treatment. In some such embodiments, the phone-based program includes 6 to 15, preferably 12 scheduled calls over the first 3 to 8, preferably 6 months of the treatment. The topics of said scheduled calls can include cognitive behavioral coaching and nutrition coaching (See, for example, Table 2). In some such embodiments, the phone-based program includes 6 to 15, preferably 12 additional calls over the next 3 to 8, preferably 6 months of treatment.

In some embodiments, the phone-based program optionally comprises on-line coaching tools, such as an integrated web support for web coaching, including the web-based program described above. The web coaching can include the essential practices for weight loss and maintaining weight loss, progress tracking, and/or virtual coaching. Non-limiting examples of the essential practices can include E-lessons, videos and podcasts, articles and games relating to topics such as healthy cooking, setting realistic goals, and controlling stress. Non-limiting examples of items the progress trackers can track include weight, nutrition intake, activity, stress, biometrics, coaching calls, etc. Non-limiting example of virtual coating can include generating and updating of to-do list for a subject participating in the program, sending emails, etc.

In some embodiments, the phone-based program can also optionally include one or more electronic devices for wireless activity monitoring. Non-limiting example of such electronic device is FitLinxx® ActiPed to be used in conjunction with a USB access point to track steps, distance, calories and activity time. The electronic device(s) can be wirelessly synced with the web support. In one embodiment, the phone-based program is the Weight Talk® Program available from Alere™.

A subject receiving the treatment of naltrexone and bupropion can enroll in the phone-based program via various methods, including both web enrollment and phone enrollment. In some embodiments, the phone-based program also include frontline support to identify patients who qualify for the clinical study, discuss benefit of the phone-based program, set realistic expectations, assist in enrollment and refer specific question to coaches.

TABLE 2

Exemplary Phone-based Weight Management Program Call Topics

| Call # | Call Topics |
| --- | --- |
| Call 1: | Getting Started: Core Values, goal setting and tracking |
| Call 2: | Reducing calories and healthy eating (with registered dietitian) |
| Call 3: | Increasing physical activity |
| Call 4: | Managing stress |
| Call 5: | Changing unhelpful thoughts |
| Call 6: | Gaining control of your environment (with registered dietitian) |
| Call 7: | Developing time management skills and improving sleep |
| Call 8: | Navigating difficult situations: social situations and restaurants |
| Call 9: | Weight maintenance skills |
| Call 10: | Rebounding from lapses |
| Call 11: | Maintaining motivation |
| Call 12: | Evaluation and Participant Feedback |

In a preferred embodiment, treatment with a combination of naltrexone sustained-release (SR)/bupropion SR (NB), alone or in conjunction with a web-based and/or telephone-based weight management program, does not increase, or more preferably decreases, the occurrence of major adverse cardiac events, defined as cardiovascular death, nonfatal myocardial infarction, or nonfatal stroke in overweight and obese subjects, as compared to placebo or a web-based and/or telephone-based weight management program alone. In some embodiments, treatment with NB, alone or in conjunction with a web-based and/or telephone-based weight management program, does not increase, or more preferably decreases, the occurrence of one or more of cardiovascular death, nonfatal myocardial infarction, nonfatal stroke, or nonfatal unstable angina requiring hospitalization in overweight and obese subjects, as compared to placebo or a web-based and/or telephone-based weight management program alone. In some embodiments, treatment with NB, alone or in conjunction with a web-based and/or telephone-based weight management program, does not increase, or more preferably decreases, one or more of: the occurrence of all cause mortality; the occurrence of unstable angina requiring hospitalization; and the occurrence of coronary revascularization procedures, as compared to placebo or a web-based and/or telephone-based weight management program alone. In some embodiments, treatment with NB, alone or in conjunction with a web-based and/or telephone-based weight management program, decreases body weight or improves systolic and/or diastolic blood pressure, as compared to placebo or a web-based and/or telephone-based weight management program alone. In some embodiments, the individual treated is overweight or obese, and at increased risk of adverse cardiovascular outcomes.

In some embodiments, treatment with a combination of naltrexone sustained-release (SR)/bupropion SR (NB), alone or in conjunction with a web-based and/or telephone-based weight management program, increases one or more of: the percent change in body weight from baseline; the percentage of subjects achieving a loss of at least 5%, 10%, and 15% of baseline body weight; and the absolute change in body weight from baseline, compared to Usual Care (no study medication and minimal lifestyle intervention program). In some embodiments, treatment with NB, alone or in conjunction with a web-based and/or telephone-based weight management program, improves one or more of: cardiovascular risk factors (one or more of waist circumference, fasting triglycerides, fasting LDL cholesterol, and fasting HDL cholesterol); vital signs (one or more of systolic and/or diastolic blood pressure, and heart rate); measures of glucose metabolism (one or more of fasting glucose, fasting insulin, and HOMA-IR); measurements derived from patient reported outcomes (one or more of eating behavior (e.g. BES), sexual function (e.g. ASEX Scale), and weight-related quality of life (e.g. IWQOL-Lite)), as compared to Usual Care (no study medication and minimal lifestyle intervention program). In some embodiments, the above mentioned increases or improvements are measured at week 26 of treatment in comparison to baseline, in some embodiments the measurements are at week 52 or 78 of treatment in comparison to baseline. In some embodiments that treated individual is female or male, 18 to 60 years, inclusive, of age, with a BMI≥30 and ≤45 kg/m$^2$ for subjects with uncomplicated obesity, and a BMI of ≥27 and ≤45 kg/m$^2$ for subjects who are overweight or obese and have dyslipidemia and/or controlled hypertension. In some embodiments the treated individual is overweight or obese, and at increased risk of adverse cardiovascular outcomes. In some embodiments, the treated individual is not overweight or obese, and at increased risk of adverse cardiovascular outcomes.

In some embodiments, treatment with a combination of naltrexone sustained-release (SR)/bupropion SR (NB), in conjunction with a web-based and/or telephone-based weight management program, is the same or increases one or more of: the percent change in body weight from baseline; the percentage of subjects achieving a loss of at least 5%, 10%, and 15% of baseline body weight; and the absolute change in body weight from baseline, compared to NB in conjunction with an intensive behavioral modification (BMOD) program for weight loss delivered in person. In some embodiments, treatment with NB, alone or in conjunction with a web-based and/or telephone-based weight management program, is the same or improves one or more of: cardiovascular risk factors (one or more of waist circumference, fasting triglycerides, fasting LDL cholesterol, and fasting HDL cholesterol); vital signs (one or more of systolic and/or diastolic blood pressure, and heart rate); measures of glucose metabolism (one or more of fasting glucose, fasting insulin, and HOMA-IR); measurements derived from patient reported outcomes (one or more of eating behavior (e.g. BES), sexual function (e.g. ASEX Scale), and weight-related quality of life (e.g. IWQOL-Lite)), as compared to NB in conjunction with an intensive behavioral modification (BMOD) program for weight loss delivered in person. In some embodiments, the above mentioned increases or improvements are measured at week 26 of treatment in comparison to baseline, in some embodiments the measurements are at week 52 or 78 of treatment in comparison to baseline. In some embodiments that treated individual is female or male, 18 to 60 years, inclusive, of age, with a BMI≥30 and ≤45 kg/m$^2$ for subjects with uncomplicated obesity, and a BMI of ≥27 and ≤45 kg/m$^2$ for subjects who are overweight or obese and have dyslipidemia and/or controlled hypertension. In some embodiments the treated individual is overweight or obese, and at increased risk of adverse cardiovascular outcomes. In some embodiments, the treated individual is not overweight or obese, and at increased risk of adverse cardiovascular outcomes.

In some embodiments, the individual has a body mass index (BMI) of at least 25 kg/m$^2$. In some embodiments, the individual has a BMI of at least 30 kg/m$^2$. In some embodiments, the individual has a BMI of at least 40 kg/m$^2$. In some embodiments, the individual has a BMI of less than 25 kg/m$^2$, or develops a BMI less than 25 kg/m$^2$ during the course of administration of naltrexone and bupropion. In these embodiments, it may be beneficial for health or cosmetic purposes to mitigate subsequent weight gain or to promote weight loss, thereby reducing the BMI even further. In some embodiments, the individual has been diagnosed by a physician as being overweight or obese. In some embodiments, the individual is identified, including self-identified, as overweight or obese, or is identified as having been diagnosed as overweight or obese. In some embodiments, the individual is suffering from dyslipidemia and/or controlled hypertension in addition to being overweight, or in addition to being obese.

In some embodiments, the promotion of weight loss is measured by a percent change from a baseline body weight. In some of these embodiments, the amount of weight loss is, is about, is at least, is at least about 0.5%, 1%, 1.5%, 2%, 2.5%, 3%, 4%, 5%, 6%, 7%, 8%, 9%, 10%, 12%, 15%, or more of initial body weight, or a range defined by any two of the preceding values. In some embodiments, the promotion of weight loss is measured as a reduction in weight gain relative to the amount of weight gain experienced by the relevant control, and the amount of reduction in weight gain is, is about, is at least, is at least about, 2%, 5%, 10%, 15%, 20%, 25%, 30%, 40%, 50%, 60%, 70%, 80%, 90%, 100%, 105%, 110%, 115%, 120%, or more, or a range defined by any two of the preceding values.

In some embodiments, the dosage is adjusted so that the patient loses weight at a rate of about 3% of baseline body weight every six months. However, the rate of weight loss for a patient may be adjusted by the treating physician based on the patient's particular needs.

In some embodiments, the mitigation of weight gain or promotion of weight loss occurs by increasing satiety in the individual. In some embodiments, the mitigation of weight gain or promotion of weight loss occurs by suppressing the appetite of the individual. In some embodiments, the treatment comprises instituting a regimen of diet and/or increased activity.

In some embodiments, the naltrexone or combination therapy, including naltrexone in combination with bupropion or fluoxetine, is in an amount sufficient to affect weight loss, reduce a cardiovascular risk factor, increase insulin sensitivity, reduce food cravings, treat a visceral fat condition, mitigate weight gain or promote weight loss during smoking cessation, or provide weight loss therapy in patients with major depression. Non-limiting examples of such methods of treatment are disclosed in U.S. Pat. Nos. 7,375,111 and 7,462,626; in U.S. Patent Publication Nos. 2007/0275970, 2007/0270450, 2007/0117827, 2007/0179168, 2008/0214592, 2007/0128298, and 2007/0129283; in U.S. patent application Ser. Nos. 12/751,970, 61/167,486, and 61/293,844; and in WO 2009/158114, each of which is hereby incorporated herein by reference in their entirety and for all purposes, including without limitation for the purpose of describing methods of affecting weight loss, reducing cardiovascular risk factors, increasing insulin sensitivity, reducing food cravings, treating visceral fat conditions, mitigating weight gain or promoting weight loss during smoking cessation, and providing weight loss therapy in patients with major depression. In some embodiments, the cardiovascular risk factor includes one or more of the following: total cholesterol level, LDL cholesterol level, HDL cholesterol level, triglyceride level, glucose level, and insulin level. In some embodiments, the cardiovascular risk factor includes one or more of the following: total cholesterol level, HDL cholesterol level, and triglyceride level.

In some embodiments, the increased efficacy of a weight loss treatment described herein comprises an improvement in an outcome measure. For example, in some embodiments, the increased efficacy increases the amount of weight loss. In some embodiments, the increase in efficacy decreases the frequency or severity of adverse events, including but not limited to nausea, constipation, vomiting, dizziness, dry mouth, headache, and insomnia. In some embodiments, the increased efficacy improves another secondary endpoint, including but not limited to waist circumference, high-sensitivity C-reactive protein (hs-CRP) levels, triglyceride levels, HDL cholesterol levels or the ratio of LDL/HDL cholesterol levels. As one of skill in the art recognizes, in some circumstances, it is desirable to decrease waist circumference, hs-CRP levels, triglyceride levels, and the ratio of LDL/HDL cholesterol levels, and to increase HDL cholesterol levels. In some embodiments, the improvement in the outcome measure is, is about, is at least, or is at least about 1, 2, 3, 4, 5, 7, 10, 12, 15, 20 30, 40, 50, 60, 70, 80, 90, or 100%, or within a range defined by any two of these values as compared to baseline or the relevant control.

In some embodiments, naltrexone or naltrexone and bupropion are each administered once per day. In some embodiments, naltrexone and bupropion are each divided into equal doses and administered more than once per day. In some embodiments, naltrexone and bupropion are each divided into unequal doses and administered more than once per day. In some embodiments, naltrexone and bupropion are divided into a different number of doses and are administered a different number of times per day. In one such embodiment, the dose of one of naltrexone or bupropion is divided, while the dose of the other is not.

In some embodiments, one or both of naltrexone and bupropion is administered one, two, three, four, or more times per day. Either or both compounds can be administered less than once per day, for example once every 2, 3, 4, 5, 6, 7, 8, 9, 10, 11, 12, 13, or 14 days, or every 1 or 2 weeks, or a range defined by any two of the preceding values. In some embodiments, the number of administrations per day is constant (e.g., one time per day). In other embodiments, the number of administrations is variable. The number of administrations may change depending on effectiveness of the dosage form, observed side effects, external factors (e.g., a change in another medication), or the length of time that the dosage form has been administered.

In some embodiments, the daily dose of naltrexone can range from about 4 mg to about 50 mg, or about 4 mg to about 32 mg, or about 8 mg to about 32 mg, or about 8 mg to about 16 mg. In some embodiments, the daily dose is about 4 mg, about 8 mg, about 12 mg, about 16 mg, about 32 mg, or about 48 mg of naltrexone, or a range defined by any two of the preceding values. The selection of a particular dosage may be based on the weight of the patient. The selection of a particular dosage may be based on the identity, dosage, and/or dosing schedule of another co-administered compound. However, in some embodiments, it may be necessary to use dosages outside these ranges. In some embodiments, the daily dose is administered in a single oral dosage form. In some embodiments, the daily dose of naltrexone is the same, and in some embodiments, the daily dose is different.

In some embodiments, the daily dose of bupropion can range from about 30 mg to about 500 mg, or about 30 mg to about 360 mg, or about 90 mg to about 360 mg. In some embodiments, the daily dose is about 30 mg, about 90 mg, about 180 mg, about 360 mg, or about 450 mg of bupropion, or a range defined by any two of the preceding values. The selection of a particular dosage may be based on the weight of the patient. The selection of a particular dosage may be based on the identity, dosage and/or dosing schedule of another co-administered compound. However, in some embodiments, it may be necessary to use dosages outside these ranges. In some embodiments, the daily dose is administered in a single oral dosage form. In some embodiments, the daily dose of bupropion is the same, and in some embodiments, the daily dose is different.

The compositions described herein may be distributed, provided to a patient for self-administration, or administered to an individual. In some embodiments, the combined naltrexone/bupropion therapies include a third compound.

In some embodiments, naltrexone and/or bupropion are provided or administered as an oral dosage form. In some embodiments, the oral dosage form is in the form of a pill, tablet, core, capsule, caplet, loose powder, solution, or suspension. In a preferred embodiment, the oral dosage form is in the form of a pill, tablet, or capsule. In some embodiments, the combined naltrexone/bupropion therapy is provided in a single oral dosage form. In some embodiments, the oral dosage form is in the form of a trilayer tablet as described in U.S. Patent Publication No. 2008/0113026, which is incorporated herein by reference in its entirety and for all purposes, including without limitation for the purpose of describing trilayer tablets, methods of making and formulating trilayer tablets, and methods of administering them.

In some embodiments, at least one of naltrexone and bupropion is administered with varying frequency during treatment. In some of these embodiments, the varying frequency comprises a decreased frequency over time. For example, one or both of naltrexone and bupropion can be initially administered more than once per day, followed by administration only once per day at a later point in treatment. In some embodiments, the daily dosage of at least one of naltrexone and bupropion is consistent despite the varying frequency of administration. For example, in some embodiments, two tablets of each of naltrexone and bupropion are initially administered twice per day, while four tablets of each of naltrexone and bupropion are administered once per day at a later point in treatment. Alternatively, in some embodiments, one or two tablets of each of naltrexone and bupropion are administered at a later point in treatment, where the one or two tablets have an equivalent total daily dosage as the two tablets each of naltrexone and bupropion initially administered twice per day.

In some embodiments where one or both of naltrexone and bupropion are administered less than once per day in a controlled release or sustained release (SR) formulation, the dose is selected so that the patient receives a daily dose that is about the same as a daily dose described herein.

In some embodiments, the naltrexone, alone or in a combination treatment, is not a sequestered form of naltrexone. For example, in some embodiments, naltrexone is in a non-sequestered, controlled release formulation. In some embodiments, naltrexone is a non-sequestered, sustained release formulation. In preferred embodiments, at least 50% of the naltrexone is released within 24 hours of administration.

In some embodiments, at least one of naltrexone or bupropion is administered in consistent daily dosages throughout the period of treatment. In some embodiments, at least one of naltrexone or bupropion is administered in varying daily dosages during the period of treatment. In some of these embodiments, the daily dosages comprise increasing daily dosages over time. In some of these embodiments, the daily dosages comprise decreasing daily dosages over time.

In some embodiments, naltrexone and bupropion are administered individually. In some embodiments, naltrexone and bupropion are administered in a single pharmaceutical composition comprising naltrexone and bupropion. In some embodiments, at least one of naltrexone or bupropion is in a sustained release or controlled release formulation. For example, sustained release forms of naltrexone are described in U.S. Patent Publication No. 2007/0281021, which is incorporated herein by reference in its entirety and for all purposes, including without limitation for the purpose of describing sustained release forms of naltrexone and bupropion, methods of making and formulating them into suitable dosage forms, and methods of administering them. In some embodiments, at least one of naltrexone or bupropion is administered with a physiologically acceptable carrier, diluent, or excipient, or a combination thereof. Non-limiting examples of naltrexone/bupropion combinations, formulations thereof, and methods of administering them are disclosed in U.S. Pat. Nos. 7,375,111 and 7,462,626, both of which are incorporated herein by reference in their entirety and for all purposes, including without limitation for the purpose of describing combinations of naltrexone and bupropion, methods of making and formulating them into suitable dosage forms, and methods of administering them. Reference herein to the use or administration of naltrexone and naltrexone/bupropion combinations is understood to include all modes of administration disclosed or referred to herein, including without limitation separate administration, administration in a single dosage form, administration in the form of salts, and/or metabolites, and/or administration in sustained release forms. Techniques for formulation and administration of the compounds of the instant application may be found in "Remington's Pharmaceutical Sciences," Mack Publishing Co., Easton, Pa., 18th edition, 1990, which is incorporated herein by reference in its entirety.

In some embodiments, naltrexone is administered prior to bupropion. In some embodiments, naltrexone is administered subsequent to bupropion. In some embodiments, naltrexone and bupropion are co-administered. As used herein, co-administration includes administration in a single dosage form, or separate dosage forms that are administered at, or nearly at, the same time.

In some embodiments, the administration of naltrexone and bupropion is continued for a period of, or of about, 1, 2, 3, 4, 6, 8, 10, 12, 16, 20, 24, 36, 48, or 52 weeks, or a range defined by any two of the preceding values. In some embodiments, the administration of naltrexone and bupropion is continued until the reduction in symptoms of a disease, disorder, or condition is stabilized for a period of, or of about, 1, 2, 3, 4, 5, 6, or more weeks, or a range defined by any two of the preceding values. For example, in some embodiments, the administration of a combined naltrexone/bupropion therapy is continued until the mitigation of weight gain or promotion of weight loss in an individual is stabilized for a period of, or of about, 1, 2, 3, 4, 5, 6, or more weeks, or a range defined by any two of the preceding values. In some embodiments, administration of naltrexone, or naltrexone and bupropion, is continued until the individual no longer needs a treatment.

In some embodiments, "administering" a drug includes an individual obtaining and taking a drug on their own. For example, in some embodiments, an individual obtains a drug from a pharmacy and self-administers the drug in accordance with the methods provided herein.

In some embodiments, the present invention relates to a kit. The kit may include one or more unit dosage forms comprising naltrexone, bupropion, or naltrexone and bupropion. The unit dosage forms may be of an oral formulation. For example, the unit dosage forms may comprise pills, tablets, or capsules. The kit may include a plurality of unit dosage forms. In some embodiments, the unit dosage forms are in a container. In some embodiments, the dosage forms are single oral dosage forms comprising naltrexone and bupropion or pharmaceutically acceptable salts thereof.

The methods, compositions and kits disclosed herein may include information. The information may be in a form prescribed by a governmental agency regulating the manufacture, use, or sale of pharmaceuticals, which notice is reflective of approval by the agency of the form of the drug for human or veterinary administration. Such information, for example, may be the labeling approved by the U.S. Food and Drug Administration for prescription drugs, or the approved product insert. The information can include required information regarding dose and dosage forms, administration schedules and routes of administration, adverse events, contraindications, warning and precautions, drug interactions, and use in specific populations (see, e.g., 21 C.F.R. § 201.57 which is incorporated herein by reference in its entirety), and in some embodiments is required to be present on or associated with the drug for sale of the drug. Dosage forms comprising a sustained-release naltrexone formulation of the invention formulated in a compatible pharmaceutical carrier may also be prepared, placed in an appropriate container, and labeled for treatment of an indicated condition. In some embodiments, a kit is for sale of a prescription drug requiring the approval of and subject to the regulations of a governmental agency, such as the Food and Drug Administration of the United States. In some embodiments, the kit comprises the label or product insert required by the agency, such as the FDA, for sale of the kit to consumers, for example in the U.S.

The information may comprise instructions to administer the unit dosage form at a dosage of about 4 mg, about 8 mg, about 12 mg, about 16 mg, about 32 mg, or about 48 mg of naltrexone or a pharmaceutically acceptable salt thereof. The information may comprise instructions to administer the unit dosage form at a dosage of about 30 mg, about 90 mg, about 180 mg, about 360 mg, or about 450 mg of bupropion or a pharmaceutically acceptable salt thereof. These instructions may be provided in a variety of ways. The information may comprise instructions about when to administer the unit dosage forms. For example, the information may comprise instructions about when to administer the unit dosage forms relative to the administration of another medication or food. In preferred embodiments, the information instructs an individual to take naltrexone, or naltrexone and bupropion, with food, preferably a meal.

Some embodiments include information, preferably printed, that taking naltrexone or a pharmaceutically acceptable salt thereof with food results in an increase in the bioavailability of naltrexone or a pharmaceutically acceptable salt thereof compared to taking the same amount of naltrexone or a pharmaceutically acceptable salt thereof without food. Some embodiments include information, preferably printed, that taking bupropion or a pharmaceutically acceptable salt thereof with food results in an increase in the bioavailability of bupropion or a pharmaceutically acceptable salt thereof compared to taking the same amount of bupropion or a pharmaceutically acceptable salt thereof without food. Some embodiments include information, preferably printed, that taking naltrexone and bupropion, or a pharmaceutically acceptable salts thereof, with food results in an increase in the bioavailability of naltrexone and/or bupropion, or a pharmaceutically acceptable salts thereof, compared to taking the same amount of naltrexone and bupropion, or a pharmaceutically acceptable salts thereof, without food. Some embodiments include information, preferably printed, that taking naltrexone, and/or bupropion or pharmaceutically acceptable salts thereof with food results in fewer or less severe drug associated adverse events than taking the same amount of naltrexone and bupropion, or a pharmaceutically acceptable salts thereof, without food. In some embodiments, the adverse events are gastrointestinal events. In some embodiments, information regarding bioavailability, adverse events, or instructions on administration regimes are provided to a subject, a dosage form comprising the medication described in the information is provided to the subject, and the dosage form is administered in accordance to the information. In some embodiments the subject is a patient in need of the medication. In some embodiments the medication is administered as a therapy for a disease as described herein.

In some embodiments, the methods, compositions and kits disclosed herein may include information regarding enrolling and/or accessing a web-based and/or telephone-based weight management program. In some embodiments, the enrollment in a web-based and/or telephone-based weight management program is a requirement of obtaining the treatment medication. In some embodiments, the enrollment in a web-based and/or telephone-based weight management program is permitted only after obtaining a prescription for the treatment medication or the actual medication. In some embodiments, the method of treatment comprises enrolling in a web-based and/or telephone-based weight management program prior to and/or as a condition of receiving the treatment medication. In some embodiments, the information includes a unique login or enrollment key for enrolling and/or accessing a web-based and/or telephone-based weight management program.

Instructions and/or information may be present in a variety of forms, including printed information on a suitable medium or substrate (e.g., a piece or pieces of paper on which the information is printed), computer readable medium (e.g., diskette, CD, etc. on which the information has been recorded), or a website address that may be accessed via the internet. Printed information may, for example, be provided on a label associated with a drug product, on the container for a drug product, packaged with a drug product, or separately given to the patient apart from a drug product, or provided in manner that the patient can independently obtain the information (e.g., a website). Printed information may also be provided to a medical caregiver involved in treatment of the patient. In some embodiments, the information is provided to a person orally.

Some embodiments comprise a therapeutic package suitable for commercial sale. Some embodiments comprise a container. The container can be in any conventional shape or form as known in the art which is made of a pharmaceutically acceptable material, for example a paper or cardboard box, a glass or plastic bottle or jar, a re-sealable bag (e.g., to hold a "refill" of tablets for placement into a different container), or a blister pack with individual dosages for pressing out of the pack according to a therapeutic schedule. The container employed can depend on the exact dosage form involved, e.g., a conventional cardboard box would not generally be used to hold a liquid suspension. It is feasible that more than one container can be used together in a single package to market a single dosage form. For example, tablets may be contained in a bottle which is in turn contained within a box. Non-limiting examples of packs and dispensers as well as oral dosage forms are disclosed in U.S. Patent Publication Nos. 2008/0110792 and 2008/0113026, both of which are hereby incorporated herein by reference in their entirety and for all purposes, including without limitation for the purpose of describing combinations of naltrexone and bupropion, methods of making and formulating them into suitable dosage forms, methods of packing and dispensing them, and methods of administering them.

The information can be associated with the container, for example, by being: written on a label (e.g., the prescription label or a separate label) adhesively affixed to a bottle containing a dosage form described herein; included inside a container as a written package insert, such as inside a box which contains unit dose packets; applied directly to the container such as being printed on the wall of a box; or attached as by being tied or taped, e.g., as an instructional card affixed to the neck of a bottle via a string, cord or other line, lanyard or tether type device. The information may be printed directly on a unit dose pack or blister pack or blister card.

The term "bupropion" may be used in a general way herein to refer to a free base of bupropion, a pharmaceutically acceptable bupropion salt (including anhydrous forms, e.g., anhydrous bupropion), a bupropion metabolite (e.g., hydroxybupropion, threohydrobupropion, and erythrohydrobupropion), a bupropion isomer, or mixtures thereof.

The term "naltrexone" may be used in a general way herein to refer to a free base of naltrexone, a pharmaceutically acceptable naltrexone salt (including hydrates and anhydrous forms, e.g., naltrexone hydrochloride dihydrate and anhydrous naltrexone hydrochloride), a naltrexone metabolite, a naltrexone isomer, or mixtures thereof.

The term "pharmaceutically acceptable salt," as used herein, refers to a formulation of a compound that does not cause significant irritation to an organism to which it is administered and does not abrogate the biological activity and properties of the compound. Pharmaceutical salts can be obtained by routine experimentation. Non-limiting examples of pharmaceutically acceptable salts include bupropion hydrochloride, radafaxine hydrochloride, naltrexone hydrochloride, and 6-β naltrexol hydrochloride.

Throughout the present disclosure, when a particular compound is mentioned by name, for example, bupropion or naltrexone, it is understood that the scope of the present disclosure encompasses pharmaceutically acceptable salts, esters, amides, or metabolites of the named compound. For example, in any of the embodiments herein, an active metabolite of naltrexone (e.g., 6β naltrexol) can be used in combination with, or instead of, naltrexone. In any of the embodiments herein, an active metabolite of bupropion, including S,S-hydroxybupropion (i.e., radafaxine), can be used in combination with, or instead of, bupropion.

The term "sustained release," as used herein, has its ordinary meaning as understood by those skilled in the art and thus includes, by way of non-limiting example, the controlled release of a drug from a dosage form over an extended period of time. For example, in some embodiments, sustained-release dosage forms are those that have a release rate that is slower that of a comparable immediate release form, e.g., less than 80% of the release rate of an immediate-release dosage form.

An immediate-release naltrexone formulation appropriate for use as a reference standard is the immediate-release naltrexone formulation, widely available commercially as the REVIA® brand of naltrexone hydrochloride, or an equivalent thereof. An immediate-release bupropion formulation appropriate for use as a reference standard is the immediate-release bupropion formulation, widely available commercially as the WELLBUTRIN® brand of bupropion, or an equivalent thereof. The U.S. government regulates the manner in which prescription drugs can be labeled and thus reference herein to the REVIA® brand of naltrexone hydrochloride and WELLBUTRIN® brand of bupropion have well-known, fixed, and definite meanings to those skilled in the art.

The term "oral dosage form," as used herein, has its ordinary meaning as understood by those skilled in the art and thus includes, by way of non-limiting example, a formulation of a drug or drugs in a form administrable to a human, including pills, tablets, cores, capsules, caplets, loose powder, solutions, and suspensions.

The terms "mitigate" or "mitigation" of weight gain, as used herein, include preventing or decreasing the amount of weight gain associated, e.g., with the administration of a drug or a change in life activity. In some embodiments, mitigation of weight gain is measured relative to the amount of weight gain typically experienced when only one or neither of naltrexone or bupropion is administered.

The term "promotion" of weight loss, as used herein, includes causing weight loss relative to a baseline weight for a least a portion of the period of treatment. This includes an individual that initially gains some weight, but during the course of treatment loses weight relative to a baseline prior to beginning treatment, as well as individuals that regain a portion or all of the weight that is lost by the end of the treatment period. In a preferred embodiment, at the end of the treatment period, the individual has lost weight relative to a baseline. In a preferred embodiment, mitigation of weight gain or promotion of weight loss in a patient administered naltrexone and bupropion is greater than when neither or only one of naltrexone or bupropion is administered, and more preferably an at least additive, or better than additive, or synergistic, effect of administering the two compounds is achieved.

In any of the embodiments described herein, methods of treatment can alternatively entail use claims, such as Swiss-type use claims. For example, a method of treating overweight or obesity with a composition can alternatively entail the use of a composition in the manufacture of a medicament for the treatment of overweight or obesity, or the use of a composition for the treatment of overweight or obesity.

It is understood by those of skill in the art that numerous and various modifications can be made without departing from the spirit of the present invention. Therefore, it should be clearly understood that the embodiments of the present invention disclosed herein are illustrative only and are not intended to limit the scope of the present invention. Any reference referred to herein is incorporated by reference for the material discussed herein, and in its entirety.

EXAMPLES

The examples below are non-limiting and are merely representative of various aspects of the invention.

Example 1 summarizes the protocol for a clinical study demonstrating that treatment with Naltrexone SR/Bupropion SR does not increase or decreases the occurrence of Major Adverse Cardiovascular Events (MACE) in overweight and obese subjects with cardiovascular risk factors.

EXAMPLES

The examples below are non-limiting and are merely representative of various aspects of the invention.

Example 1 summarizes the protocol for a clinical study demonstrating that treatment with Naltrexone SR/Bupropion SR does not increase or decreases the occurrence of Major Adverse Cardiovascular Events (MACE) in overweight and obese subjects with cardiovascular risk factors.

Example 1

Title

A Multicenter, Randomized, Double-Blind, Placebo-Controlled Study Assessing the Occurrence of Major Adverse Cardiovascular Events (MACE) in Overweight and Obese Subjects With Cardiovascular Risk Factors Receiving Naltrexone SR/Bupropion SR Primary Objective Demonstrate that 32 mg naltrexone sustained-release (SR)/360 mg bupropion SR (NB32) is no worse, or better compared to placebo on the occurrence of MACE, defined as cardiovascular death, nonfatal myocardial infarction, or nonfatal stroke in overweight and obese subjects.

Secondary Objectives

Demonstrate NB32 is no worse or better compared to placebo on the occurrence of cardiovascular death, nonfatal myocardial infarction, nonfatal stroke, or nonfatal unstable angina requiring hospitalization in overweight and obese subjects.

Demonstrate NB32 is no worse or better compared to placebo on the occurrence of each of the components of the primary objective in overweight and obese subjects.

Other Objectives

Demonstrate that NB32 no worse or better than placebo on:
  the occurrence of all cause mortality
  the occurrence of unstable angina requiring hospitalization
  the occurrence of coronary revascularization procedures
  change in body weight
  change in systolic and diastolic blood pressure Study Design This is a multicenter, randomized, double-blind, placebo-controlled study measuring the occurrence of MACE in overweight and obese subjects at increased risk of adverse cardiovascular outcomes receiving NB32.

Approximately 9,880 subjects are enrolled into a double-blind lead-in period to identify subjects who do not tolerate treatment with low dose NB well or who exhibit other characteristics predictive of lack of compliance. At initiation of the lead-in period, subjects are randomly assigned in a 1:1 ratio to one of two treatment sequences: 1 week of active study medication (1 tablet per day) followed by 1 week of placebo (1 tablet per day), or 1 week of placebo followed by 1 week of active study medication. Eligible subjects are subsequently randomized to treatment with either NB32 or placebo in a 1:1 ratio. The duration of the randomized treatment period (or subject follow-up period for those who discontinue study medication early) is estimated to be between 2-4 years for most subjects.

Subject enrollment may occur in two stages, with approximately 6,850 subjects enrolled to support accrual of sufficient events in randomized subjects for the interim analysis, and approximately 3,030 subjects subsequently enrolled to complete the study. Events in randomized subjects from both stages of enrollment support the final analysis. Additional subjects may be recruited if withdrawal rates during the lead-in period are greater than anticipated.

The study is conducted at approximately 300 centers.

The study consists of three periods:

1) Screening Period (starting at Visit 1, Screen, with informed consent): up to 2 weeks to verify eligibility prior to the first dose of study medication in the lead-in period.

2) Lead-in Period (starting at Visit 2, Week −2): double-blind, 2-week period during which the subjects receive treatment according to one of two sequences: 1 week of active study medication (8 mg naltrexone SR/90 mg bupropion SR [NB]) once a day followed by 1 week of placebo once a day; or 1 week of placebo followed by 1 week of active study medication. Subjects are randomly assigned to NB or placebo for the lead-in period using a centralized Interactive Voice or Web Response System (IVRS/IWRS). Subjects are also required to record dietary intake information daily during this 2-week lead-in period. Regular use of food diaries (e.g., entries logged for a minimum of 10 out of 14 days) and study medication compliance (e.g., 10 out of 14 pills taken) is required for randomization to treatment. Subjects who discontinue study medication treatment or who had a suspected MACE event during the lead-in period are not eligible for randomization to treatment or participation in subsequent study procedures.

3) Treatment Period (starting at Visit 3, Day 1): double-blind, randomized period during which the subjects who completed the lead-in period and satisfied inclusion/exclusion criteria receive active study medication or placebo. The treatment period starts upon randomization at Visit 3 (Day 1). Randomized treatment assignment is via a centralized IVRS/IWRS. Each site is identified by a unique number, and each subject has a unique identifier assigned.

a) At Visit 6 (Week 16) there is an evaluation of weight loss and blood pressure changes relative to baseline observations. The target weight loss is ≥5% with expected minimum weight loss at 16 weeks of ≥2%. Subjects should be discontinued from study medication at Week 16 if:
    they have not lost at least 2% of their body weight or
    they are experiencing sustained (e.g., at 2 or more visits) increases in blood pressure (systolic or diastolic) of ≥10 mm Hg. If the Investigator suspects that an elevated blood pressure measurement may be spurious, subjects should not be discontinued until the elevated measurement is confirmed within 4 weeks.

b) All subjects participate in a comprehensive web-based weight management program as detailed above. Subjects participate in the weight management program through completion of study procedures, regardless of whether they are taking study medication.

c) Every other month between visits past Visit 7 (Week 26), subjects are asked to answer specific questions pertaining to compliance and hospitalizations (potential MACE or serious adverse events [SAEs]), using an internet- or telephone-based data collection system.

d) All randomized subjects who discontinue study medication early complete the End-of-Treatment Visit procedures and continue to participate in the study for the remainder of the trial for collection of MACE data. Subjects are asked to come to the study site at their scheduled visits and complete the internet- or telephone-based data collection every other month between visits past Visit 7 (Week 26) even though they are no longer taking study medication.

Study Population

Overweight and obese subjects at increased risk of adverse cardiovascular outcomes are eligible to participate in this study. Approximately 9,880 subjects are enrolled into the double-blind lead-in period, and of those it is anticipated that 9,190 are randomized into the double-blind treatment period (i.e., approximately 7% of subjects are expected to discontinue the study during the lead-in period).

Inclusion Criteria

Subjects must meet all of the following inclusion criteria to be eligible for participation in this study.
1. ≥50 years of age (women) or ≥45 years of age (men)
2. Body mass index (BMI)≥27 kg/m2 and ≤50 kg/m2
3. Waist circumference ≥88 cm (women) or ≥102 cm (men)
4. At increased risk of adverse cardiovascular outcomes:
   a. Cardiovascular disease (confirmed diagnosis or at high likelihood of cardiovascular disease) with at least one of the following:
      History of documented myocardial infarction >3 months prior to screening
      History of coronary revascularization (i.e., coronary artery bypass graft surgery, stent placement, percutaneous transluminal coronary angioplasty, or laser atherectomy)
      History of carotid or peripheral revascularization (i.e., carotid endarterectomy, lower extremity atherosclerotic disease atherectomy, repair of abdominal aorta aneurysm, femoral or popliteal bypass)
      Angina with ischemic changes (resting ECG), ECG changes on a graded exercise test (GXT), or positive cardiac imaging study
      Ankle brachial index <0.9 (by simple palpation) within prior 2 years
      ≥50% stenosis of a coronary, carotid, or lower extremity artery within prior 2 years
      and/or
   b. Type 2 diabetes mellitus with at least 2 of the following:
      Hypertension (controlled with or without pharmacotherapy at <145/95 mm Hg)
      Dyslipidemia requiring pharmacotherapy
      Documented low HDL cholesterol (<50 mg/dL in women or <40 mg/dL in men) within prior 12 months
      Current tobacco smoker.

Randomization of subjects with cardiovascular disease is targeted to be approximately 30% of all subjects randomized to study medication. Randomization of males with age ≥45 to <50 is targeted to be approximate 125% of all male subjects randomized to study medication, and randomization of females with age ≥50 to <55 is targeted to be approximately 25% of all female subjects randomized to study medication. The Data Monitoring Committee (DMC) may recommend adjusting these percentages, or other enrollment criteria, during the study conduct based on actual event rate observed and the overall distribution of the study population as it accrues.

Exclusion Criteria
1. Myocardial infarction within 3 months prior to screening
2. Angina pectoris Grade III or IV as per the Canadian Cardiovascular Society grading scheme (Table 3)
3. Clinical history of cerebrovascular disease (stroke)
4. History of tachyarrhythmia other than sinus tachycardia
5. Blood pressure ≥145/95 mm Hg, irrespective of treatment with antihypertensive agents
6. Unstable weight within 3 months prior to screening (e.g., weight gain or loss of ≥3%)
7. Planned bariatric surgery, cardiac surgery, or coronary angioplasty
8. Severe renal impairment defined by an estimated GFR<30 mL/min
9. Clinical history of liver failure or documented ALT or AST greater than 3 times the upper limit of normal (ULN)
10. Known infection with HIV or hepatitis
11. Chronic use or positive screen for opioids
12. Recent drug or alcohol abuse or dependence (with the exception of nicotine dependence) within 6 months prior to screening
13. History of seizures (including febrile seizures), cranial trauma, or other conditions that predispose the subject to seizures
14. History of mania or current diagnosis of active psychosis, active bulimia or anorexia nervosa (binge eating disorder is not exclusionary)
15. At risk for suicide attempts based on the judgment of the Investigator
16. Acute depressive illness including new onset of depression or acute exacerbation of symptoms (stable subjects on chronic treatment for depression are not excluded)
17. Any condition with life expectancy anticipated to be less than 4 years (e.g., congestive heart failure NYHA Class 3 or 4; Table 4)
18. History of malignancy within the previous 5 years, with exception of non-melanoma skin cancer or surgically cured cervical cancer
19. Current use of other bupropion or naltrexone containing products
20. History of hypersensitivity or intolerance to naltrexone or bupropion
21. Use of monoamine oxidase inhibitors within 14 days prior to screening
22. Use of any investigational drug, device, or procedure within 30 days prior to screening
23. Pregnant or breast-feeding women, or currently trying to become pregnant, or of child-bearing potential (including peri-menopausal women who have had a menstrual period within one year) and not willing to practice birth control
24. Inability to consistently access broadband internet
25. Employment by the Sponsor or the study site, or co-habitation with another individual enrolled in the study Study Medications The study medication (NB and placebo) is provided as tablets. Each active tablet contains 8 mg naltrexone SR/90 mg bupropion SR (8/90). All tablets, including placebo, are identical in appearance to maintain blinding. Dose escalation occurs during the first 4 weeks of the treatment period, as shown in the table below.

Route of Administration: Oral. Doses can be taken with or without food.

|  | Lead-in Period | | Treatment Period | | | |
| --- | --- | --- | --- | --- | --- | --- |
| Dose Schedule | Week −2 | Week −1 | Week 1 (Days 1-7) | Week 2 (Days 8-14) | Week 3 (Days 15-21) | Week 4 through end of study |
| Total Daily Dose* | 8/90 NB | 8/90 NB | 8/90 NB | 16/180 NB | 24/270 NB | 32/360 NB |
| Morning | 1 tab NB or PBO | 1 tab NB or PBO | 1 tab NB or PBO | 1 tab NB or PBO | 2 tab NB or PBO | 2 tab NB or PBO |
| Evening | — | — | — | 1 tab NB or PBO | 1 tab NB or PBO | 2 tab NB or PBO |

*Doses shown are of naltrexone SR/bupropion SR (NB); tab = tablet: PBO = placebo.

Study Procedures

See Schedule of Study Procedures (Appendix 1).

Adverse Event Collection

Potential cardiovascular events occurring during the lead-in and randomized treatment period of the study are collected and subjected to adjudication by an independent Clinical Endpoint Committee (CEC) to identify those events that meet the MACE endpoint definition. Deaths and potential cardiovascular events specified in this trial as endpoint events are exempted from the usual expedited regulatory reporting requirements, in keeping with 21 CFR 312.32(c)(5). All parties involved with the trial conduct at the site are to remain blinded to treatment assignment for subjects that have such events. Consistent with the well established general safety profile from both the NB phase 3 program and extensive clinical experience of both individual NB components, routine safety data collection is limited to adverse events leading to discontinuation of study medication and SAEs. Information on any in utero exposures and pregnancy outcomes are also collected. Safety data are reviewed on an ongoing basis by an independent DMC.

Statistical Analysis

Primary Endpoint:

Time from treatment period randomization to the first confirmed occurrence of MACE, defined as cardiovascular death, nonfatal myocardial infarction, or nonfatal stroke.

Analysis Populations and Data Considerations:

Enrolled: Subjects who take at least one dose of study medication during the lead-in period. Data from this population are not used in any formal statistical analyses.

Intent-to-treat (ITT): Subjects who undergo randomization into the treatment period and are dispensed study medication. All post-randomization data in the treatment period are included in statistical analyses for this population. The ITT population is the primary analysis population for the primary endpoint and all secondary endpoints.

Protocol: ITT subjects who take at least one dose of study medication in the treatment period in accordance with the study protocol. Data values observed up to and including 30 days after a subject's last confirmed treatment period dose date are included in all analyses for the Per Protocol population (referred to as on-treatment data), while data values outside of this window are excluded. The Per Protocol population is used for sensitivity analyses.

Hypotheses for the Primary Endpoint and Testing Procedure:

With respect to the primary endpoint, the following 3 null hypotheses are tested:

H01: The hazard ratio for NB32 relative to placebo is ≥2.0
H02: The hazard ratio for NB32 relative to placebo is ≥1.4
H03: The hazard ratio for NB32 relative to placebo is ≥1.0 (test for superiority)

In order to control the Type 1 error rate at the one-sided $\alpha=0.025$ level, a sequential testing procedure is used. The testing procedure is described below and is based on MACE confirmed by adjudication.

Accrue at least 87 events.

Conduct analysis to rule out a non-inferiority (NI) margin of 2.0 using all of alpha (testing H01).

The trial must stop if the NI margin of 2.0 is not met. Note that when the true underlying hazard ratio is equal to 1, the least favorable hazard ratio point estimate that still results in non-inferiority for this test is 1.314.

If the NI margin of 2.0 is met, all of alpha is recovered; the trial proceeds to at least 371 events to rule out the NI margin of 1.4 at the end of the study (testing H02).

The final analysis to rule out the NI margin of 1.4 is conducted using all of alpha without adjustment since it is the first analysis against the NI margin of 1.4. The first analysis with 87 events is not used to rule out the NI margin of 1.4 and hence no multiplicity control is needed between this analysis and the analyses against the NI margin of 2.0. Note that when the true underlying hazard ratio is equal to 1, the least favorable hazard ratio point estimate that will still result in non-inferiority for this test is 1.142.

If H02 is successfully rejected, the analysis proceeds to test H03 using all of alpha. This is the gated test for superiority.

Choice of NI Margin:

In a study population with an annual background MACE rate of 1.0-1.5%:

The pre-approval NI margin of 2.0 corresponds to ruling out an excess of 10-15 additional events per 1,000 subject-years with an absolute risk difference of 1.0-1.5%.

The post-approval NI margin of 1.4 corresponds to ruling out an excess of 4-6 additional events per 1,000 subject-years with an absolute risk difference of 0.4-0.6%.

Secondary Endpoints:

Time from treatment period randomization to the first confirmed occurrence of cardiovascular death, nonfatal myocardial infarction, nonfatal stroke, or nonfatal unstable angina requiring hospitalization Time from treatment period randomization to the confirmed occurrence of cardiovascular death (including fatal myocardial infarction, fatal stroke)

Time from treatment period randomization to the first confirmed occurrence of myocardial infarction (nonfatal or fatal)

Time from treatment period randomization to the first confirmed occurrence of stroke (nonfatal or fatal)

Other Endpoints:
   Time from treatment period randomization to the confirmed occurrence of death from any cause
   Time from treatment period randomization to the first confirmed occurrence of unstable angina requiring hospitalization (nonfatal or fatal)
   Time from treatment period randomization to the first occurrence of coronary revascularization procedure
   Percent change in body weight from baseline to Week 52
   Proportion of subjects achieving ≥10% body weight reduction from baseline at Week 52
   Change in blood pressure from baseline to Week 52

Sample Size:
The following assumptions were used to determine the number of confirmed MACE required for the final analysis against a NI margin of 1.4 for the primary hypothesis in the primary analysis population (ITT).
   Underlying hazard ratio of active to control: 1
   NI margin: 1.4
   One-sided α=0.025
   At least 90% power at the final analysis to establish that the upper bound of a one-sided 97.5% confidence interval for the hazard ratio will fall below the pre-specified NI margin.

Under these assumptions, the trial requires 371 events. Similarly, 87 events provides 90% power for the NI margin of 2.0.

To estimate sample size for the ITT population, the following assumptions are used in addition to those listed above. These assumptions are necessary to allow a sample size to be calculated.

However, since this is an event-driven study, the power for the study is based on the number of MACE rather than the number of subjects. The assumptions used below represent a single cohort of subjects randomized in one stage for the final analysis and do not incorporate potential variations such as enrollment of subjects in more than one stage. Accordingly, the actual sample size may vary from the sample size calculation provided in this protocol depending on the actual accrual of events.
   Recruitment period: 1.5 years
   1:1 randomization
   Maximum subject follow-up: 4 years
   Lost to follow up (LTFU) rate: 0.012 annual LTFU
   Primary MACE endpoint annualized event rate: 1.5% in the control group Under these assumptions, the trial requires N=3,955 subjects per treatment group. However, the number of subjects planned is N=4,593 per treatment group to allow for accrual of a sufficient number of events in case of minor departures from event rate, recruitment and retention rates, and underlying hazard ratio assumptions.

This event-driven study is stopped when at least 371 MACE have been confirmed. Accrual of 371 confirmed MACE provides 90% power for the primary analysis with a NI margin of 1.4 in the ITT population (H02). The least favorable hazard ratio that can still result in a non-inferiority result for H02 is 1.142 when the true underlying hazard ratio is equal to 1. With this number of events and the expected discontinuation rate from study medication, there are a sufficient number of confirmed on-treatment MACE to provide high probability that the hazard ratio estimate in the Per Protocol population is less than 1.142 assuming the true underlying hazard ratio is equal to 1. Similarly, in the analysis using a NI margin of 2.0, accrual of at least 87 confirmed MACE provides 90% power in the ITT population with the least favorable hazard ratio that can still result in a non-inferiority result for H01 being 1.314 when the true underlying hazard ratio is equal to 1. There are a sufficient number of confirmed on-treatment MACE to provide high probability that the hazard ratio estimate in the Per Protocol population is less than 1.314 assuming the true underlying hazard ratio is equal to 1.

APPENDIX 1

SCHEDULE OF STUDY PROCEDURES

| | Screening Visit 1 (Screening) | Lead-in Visit 2 (Wk −2) | Visit 3 (Day 1) (Baseline) | Visit 4 (Wk 2) | Visit 5 (Wk 8) | Visit 6 (Wk 16) | Visit 7-13 (Wks 26, 52, 78, 104, 130, 156, 182) | Visit 14 (Wk 208; End-of-Study)[5] | End of Treatment Visit[6] | Remote Contacts[7] |
|---|---|---|---|---|---|---|---|---|---|---|
| Informed Consent | X | | | | | | | | | |
| Eligibility Criteria | X | X | X (labs) | | | | | | | |
| Demographics | X | | | | | | | | | |
| Medical History | X | | | | | | | | | |
| Height | X | | | | | | | | | |
| Weight | X | X | X | X | X | X | X | X | X | |
| Waist Circumference | X | | | | | | | X | X | |
| Vital Signs (BP and HR) | X | X | X | X | X | X | X | X | X | |
| Concomitant Medications | X | | | | | | X[1] | X | X | |
| Pregnancy Test (urine)[2] | | X | | | | | | | | |
| Drug Screen (urine) | | X | | | | | | | | |
| Chemistry, Hematology, Urinalysis, Lipids, HbA1c, hsCRP | | X | | | | | | | | |
| Electrocardiogram | | X | | | | | | | | |
| Enrollment and Lead-in Randomization | | X | | | | | | | | |
| Study Training | | X | X | | | | X[3] | | | |
| Evaluation of Study Medication and Food Diary Compliance | | | X | | | | | | | |

APPENDIX 1-continued

SCHEDULE OF STUDY PROCEDURES

| | Period: | | | | | | | | |
|---|---|---|---|---|---|---|---|---|---|
| | | | Treatment | | | | | | |
| | Screening Visit 1 (Screening) | Lead-in Visit 2 (Wk −2) | Visit 3 (Day 1) (Baseline) | Visit 4 (Wk 2) | Visit 5 (Wk 8) | Visit 6 (Wk 16) | Visit 7-13 (Wks 26, 52, 78, 104, 130, 156, 182) | Visit 14 (Wk 208; End-of-Study)[5] | End of Treatment Visit[6] | Remote Contacts[7] |
| Treatment Randomization | | | X | | | | | | | |
| MACE | | | X | X | X | X | X | X | X | X |
| SAEs, AEs Leading to Discontinuation, Pregnancies | | | X | X | X | X | X | X | X | X |
| Weight Management Program | | | | | | | →  | | | |
| Evaluation to Continue Treatment | | | | | | X | | | | |
| Study Medication Dispensing/Return[4] | | X | X | | X | X | X | X | X | |
| Study Medication Compliance | | | X | X | X | X | X | X | X | X |

The visit window for Visit 3 (Day 1) is ±3 days relative to Visit 2 (Week -2). Post-baseline visit windows are ±3 days at Visit 4, ±1 week at Visit 5 and 6, ±2 weeks for subsequent visits.
[1]For Visits 8, 10, and 12 only.
[2]Women of child-bearing potential (including peri-menopausal women who have had a menstrual period within one year) only.
[3]Visit 7 training will focus on remote internet or telephone contact procedures.
[4]Visit 2 = dispensing only, Visit 14/End-of-Study Visit, and End-of-Treatment Visit = return only.
[5]Subjects with an End-of-Treatment Visit will not return study medication or have compliance or concomitant medications recorded at Visit 14/End-of-Study Visit.
[6]Subjects who discontinue study medication before Week 208 will be asked to return to the study site for the indicated end-of-treatment assessments, and asked to return for their remaining visits through Week 208 for follow-up.
[7]After Visit 7 and through the remainder of the study, subjects will answer specific questions pertaining to compliance and any occurence of hospitalization through an internet or telephone based data collection system every 2 months between visits. Hospitalization information will be used to identify potential MACE or SAEs.

Example 2 summarizes the protocol for a clinical study demonstrating the beneficial effect of Naltrexone SR/Bupropion SR on body weight and cardiovascular risk factors in overweight and obese subjects in conjunction with a comprehensive lifestyle intervention (CLI) program compared minimal lifestyle intervention program.

Example 2

Title

A Multicenter, Randomized, Open-Label, Controlled, Method-of-Use Study Assessing the Effect of Naltrexone SR/Bupropion SR on Body Weight and Cardiovascular Risk Factors in Overweight and Obese Subjects Primary Objective To assess the effect of the intended clinical method of use of 32 mg naltrexone sustained release (SR)/360 mg bupropion SR (NB) in conjunction with a comprehensive lifestyle intervention (CLI) program compared to Usual Care (minimal lifestyle intervention program) on body weight at Week 26 in subjects who are overweight with dyslipidemia and/or controlled hypertension or obese Secondary Objectives To assess the effect of NB and CLI compared to Usual Care on:

The percentage of subjects achieving a loss of at least 5%, 10%, and 15% of baseline body weight at Week 26

Changes in cardiovascular risk factors (waist circumference and lipids) at Week 26

Changes in vital signs (systolic and diastolic blood pressure and heart rate) at Week 26

Changes in measures of glucose metabolism (fasting glucose, insulin, and homeostasis model assessment—insulin resistance [HOMA-IR]) at Week 26

Changes in patient reported measures of eating behavior (Binge Eating Scale [BES]), sexual function (Arizona Sexual Experiences [ASEX] Scale), and weight-related quality of life (Impact of Weight on Quality of Life-Lite Questionnaire [IWQOL-Lite]) at Week 26.

Additional Objectives

To assess the effect of NB and CLI compared to Usual Care on change in body weight from baseline to post-baseline visits through Week 20

To assess the effect of NB and CLI compared to Usual Care on changes in patient reported measures of eating behavior, sexual function, and weight-related quality of life at Week 16

To assess the longer term effects of NB and CLI (beyond 26 weeks) on body weight, cardiovascular risk factors, vital signs, and glucose metabolism Study Design This is a Phase 3b, multicenter, randomized, open-label, controlled study to assess the effects of NB, used in a manner consistent with its intended use after marketing approval, on body weight and cardiovascular risk factors compared to the effects of Usual Care in subjects who are overweight with dyslipidemia and/or controlled hypertension or obese.

A minimum of 198 and up to 242 subjects will be randomly assigned to either NB or Usual Care in a 1.75:1 ratio across approximately 15 centers in the United States. Subjects randomized to receive NB will also participate in an internet-based CLI program that includes a progressive nutrition and exercise program with goal setting and tracking tools. Subjects randomized to receive Usual Care will participate in a minimal lifestyle intervention program consisting of periodic education/advice from study site personnel. After 26 weeks, all subjects will receive NB and CLI through Week 78.

The study consists of three periods:
1) Screening Period (starting at Visit 1): up to 2 weeks to verify eligibility prior to randomization.
2) Controlled Treatment Period ((Visit 2 [Day 1] to Visit 8 [Week 26]): open-label period during which subjects who satisfied inclusion/exclusion criteria will receive active study medication (NB) and CLI or Usual Care (no study medication and minimal lifestyle intervention program). Subjects will be randomly assigned to their treatment group using a centralized Interactive Voice or Web Response System (IVRS/IWRS).
   a) Subjects in either treatment group who discontinue from full participation will not continue with scheduled study procedures but will be instructed to return to the study site at Weeks 26, 52, and 78 to have their weight measured. Subjects randomized to NB who discontinue from full participation will also discontinue study medication but will be allowed to continue participation in the CLI program for the remainder of the study.
   b) At Visit 6 (Week 16) there will be an evaluation of weight loss and blood pressure changes relative to baseline observations for subjects randomized to NB. NB-treated subjects should be discontinued from full participation at Week 16 if:
      they have not lost at least 5% of their baseline body weight or
      they are experiencing sustained (i.e., at Visit 5 [Week 10] and Visit 6 [Week 16]) increases in blood pressure (systolic or diastolic) of ≥10 mm Hg
3) Uncontrolled Treatment Period (Visit 8 [Week 26] to Visit 15 [Week 78]): open-label treatment period.
   a) Subjects originally randomized to and still taking NB as directed will continue their study medication and continue to participate in the CLI program.
   b) Subjects originally randomized to Usual Care will switch to NB, in conjunction with CLI at Week 26. Subjects who switch to NB and CLI will follow the same NB dosing schedule, CLI curriculum, and evaluation of weight loss and blood pressure changes for continuing with therapy as subjects originally randomized to NB and CLI, only 26 weeks later in the study.
   c) Subjects who discontinue from full participation will not continue with scheduled study procedures but will be instructed to return to the study site at Weeks 52 (if applicable) and 78 to have their weight measured. Subjects who discontinue from full participation will also discontinue study medication but will be allowed to continue participation in the CLI program for the remainder of the study.

Study Population

A minimum of 198 and up to 242 overweight or obese subjects who are eligible to participate will be randomized into the study.

Inclusion Criteria

Subjects must meet all of the following inclusion criteria to be eligible for participation in this study.
1. Female or male subjects, 18 to 60 years, inclusive, of age
2. Body mass index (BMI) ≥30 and ≤45 kg/m2 for subjects with uncomplicated obesity, and BMI of ≥27 and ≤45 kg/m2 for subjects who are overweight or obese and have dyslipidemia and/or controlled hypertension Exclusion Criteria Subjects meeting any of the following exclusion criteria will not be eligible for participation in this study.
1. History of type 1 or type 2 diabetes mellitus diagnosis
2. Myocardial infarction within 6 months prior to screening (Visit 1)
3. Angina pectoris Grade III or IV as per the Canadian Cardiovascular Society grading scheme (Table 3)
4. Clinical history of large vessel cortical strokes, including ischemic and hemorrhagic strokes (i.e., transient ischemic attack is not exclusionary)
5. Blood pressure ≥145/95 mm Hg at screening (Visit 1) or randomization (Visit 2)
6. Initiation or alteration of dose of lipid-lowering agents within 4 weeks prior to screening (Visit 1)
7. History (within the last 20 years) of seizures, cranial trauma, bulimia, anorexia nervosa, or other conditions hat predispose the subject to seizures
8. Unstable weight (i.e., weight gain or loss of ≥3%) within 3 months prior to screening (Visit 1)
9. Use of prescribed or over-the-counter drugs intended for weight loss, or participation in a weight loss program within one month prior to screening (Visit 1)
10. Planned surgical or device intervention for obesity (e.g., gastric banding)
11. Current or history of severe renal impairment, defined by an estimated glomerular filtration rate (GFR)<30 mL/min/1.73 $m^2$
12. Clinical history of liver failure or current documented aspartate aminotransferase (AST) or alanine aminotransferase (ALT)>3 times the upper limit of normal (ULN) at screening (Visit 1)
13. Fasting glucose ≥126 mg/dL or fasting triglycerides ≥400 mg/dL at screening (Visit 1)
14. Current known infection with HIV or hepatitis (documentation of no detectable virus is required for subjects with a past infection of hepatitis B or C)
15. Chronic use or positive screen for opioids at screening (Visit 1)
16. Drug or alcohol abuse or dependence within 6 months prior to screening (Visit 1) or positive urine drug screen
17. Regular use of tobacco products (an average of at least 1 product per day) including inhaled tobacco (such as cigarettes, cigars, pipes, etc.), chewing tobacco or snuff, or nicotine replacement products in the 6 months prior to screening (Visit 1)
18. History of mania or current diagnosis of active psychosis
19. At risk for suicide attempts based on the judgment of the Investigator
20. Acute depressive illness, including new onset of depression or acute exacerbation of symptoms (stable subjects on chronic treatment for depression are not excluded)
21. Current use of other bupropion- or naltrexone-containing products or a history of hypersensitivity or intolerance to naltrexone or bupropion
22. Current use of anticonvulsant agents, dopamine agonists, theophylline, or oral corticosteroids or use of monoamine oxidase inhibitors within 14 days prior to screening (Visit 1)
23. Use of any investigational drug, device, or procedure within 30 days prior to screening (Visit 1)
24. Pregnant or trying to become pregnant, currently breast-feeding, or of child-bearing potential (including perimenopausal women who have had a menstrual period within one year) and not willing to practice birth control using a double barrier method (criteria apply to women only)

25. Any clinically significant electrocardiogram, laboratory, hematology, physical exam, medical history, or urinalysis finding that in the investigator's opinion should prohibit participation in the study
26. Inability or unwillingness to perform regular, moderate-intensity exercise, such as brisk walking
27. Inability to access broadband internet or email daily (analog or dial-up access is not acceptable)
28. Inability to complete a test of email use and CLI program access prior to randomization (Visit 2)
29. Inability to comply with all required study procedures and schedule, inability to speak and read English, or unwillingness or inability to give written informed consent
30. Employee or immediate family member of the Sponsor or member of the study site research staff, or cohabitation with another individual randomized in the study Study Medications
The study medication (NB) will be provided as tablets. Each tablet will contain 8 mg naltrexone SR/90 mg bupropion SR. Dose escalation will occur during the first 4 weeks of the Controlled Treatment Period for subjects initially randomized to NB and during the first 4 weeks of the Uncontrolled Treatment Period for subjects initially randomized to the Usual Care group, as shown in the table below.

Route of Administration: Oral. Doses can be taken with or without food. Tablets must be swallowed whole, and should not be cut or crushed.

| NB Dose Schedule | $1^{st}$ Week | $2^{nd}$ Week | $3^{rd}$ Week | $4^{th}$ Week to study end |
|---|---|---|---|---|
| Morning | 1 NB tablet | 1 NB tablet | 2 NB tablets | 2 NB tablets |
| Evening | — | 1 NB tablet | 1 NB tablet | 2 NB tablets |
| Total Naltrexone/Bupropion Daily Dose (mg) | 8/90 | 16/180 | 24/270 | 32/360 |

Subjects in both treatment groups will follow the same NB dose schedule but at different points in the study.
Subjects randomized to NB will initiate the NB treatment at Week 1; subjects randomized to Usual Care will initiate NB treatment at Week 26.

Study Procedures
See Schedule of Study Procedures (Appendix 2).
Statistical Analysis
Analysis Population Definitions:
Randomized: Subjects who undergo randomization into the Controlled Treatment Period.
Intent-to-Treat (ITT): Subjects randomized to NB and CLI who have received at least one dose of study medication and subjects randomized to Usual Care who have received their baseline lifestyle intervention program instruction.
Modified ITT (mITT): Subjects from the ITT population who have completed the Week 2 study visit, have a baseline body weight measurement, and have at least one postbaseline body weight measurement. Subjects randomized to the NB and CLI group must still be taking study medication at the Week 2 study visit.
Week 26 Per Protocol (PP): Subjects from the ITT population who have completed the study through Week 26 in compliance with the protocol. Subjects randomized to the NB and CLI group must have passed the evaluation of weight loss and blood pressure changes for continuing with therapy at Week 16 and still be taking study medication at the Week 26 study visit.
Week 52 Per Protocol (PP): Subjects from the Week 26 PP population who have completed the study through Week 52 (on study medication at Week 52) and in compliance with the protocol. Subjects who switched from Usual Care to NB and CLI must have passed the evaluation of weight loss and blood pressure changes for continuing with therapy at Week 42.
Week 78 Per Protocol (PP): Subjects from the Week 52 PP population who have completed the study through Week 78 (on study medication at Week 78) and in compliance with the protocol.

The primary efficacy and safety analysis populations are the Week 26 PP and ITT populations, respectively.
Primary Study Endpoint:
Percent change in body weight from baseline (Day 1) to Week 26.
Secondary Study Endpoints
Percentage of subjects achieving a loss of at least 5%, 10%, and 15% of baseline body weight at Week 26
Absolute change in body weight from baseline to Week 26
Changes in cardiovascular risk factors from baseline to Week 26, including:
Waist circumference
Fasting triglycerides
Fasting LDL cholesterol
Fasting HDL cholesterol
Changes in vital signs from baseline to Week 26, including:
Systolic and diastolic blood pressure
Heart rate
Changes in measures of glucose metabolism from baseline to Week 26, including:
Fasting glucose
Fasting insulin
HOMA-IR
Changes in measurements derived from patient reported outcomes from baseline to Week 26, including:
Eating behavior (BES)
Sexual function (ASEX Scale)
Weight-related quality of life (IWQOL-Lite)
Additional Study Endpoints
Changes in body weight, cardiovascular risk factors, vital signs, glucose metabolism, and patient reported outcomes from baseline to post-baseline visits (prior to and after Week 26, as applicable)
Changes in body weight, cardiovascular risk factors, vital signs, and glucose metabolism from baseline of Uncontrolled Treatment Period (Week 26) to post-Week 26 visits (in particular, the Week 52 and Week 78 visits).
Sample Size
The sample size was calculated by estimating the number of subjects required to have ≥90% power to detect a significant difference ($\alpha=0.05$) between the treatment groups at Week 26 for the Week 26 PP Population using a two-sample t-test with the following assumptions:
Effect size between 0.6 and 0.75, which is within the range observed in the NB Phase 3 clinical program
Overall discontinuation rate from full participation between randomization and Week 26: 60% for NB and CLI (includes discontinuation due to the Week 16 assessment) and 30% for Usual Care
A 1.75:1 randomization to account for the assumed differential rate of discontinuation from full participation for the treatment groups at Week 26
Two-sided $\alpha=0.05$
Under these assumptions, between 198 and 242 randomized subjects are required to detect a significant difference between groups for the approximately 80 to 120 subjects (39 to 60 per treatment group) expected to comprise the Week 26 PP population. The assumptions for effect size and discontinuation rates from full participation are based on data from the NB Phase 3 clinical program and scientific publications pertaining to usual care for obesity (See, Wadden, et al., "A two-year randomized trial of obesity treatment in primary care practice," N Engl J. Med. 2011, 365(21):1969-1979; Tsai, et al., "A primary care intervention for weight loss: results of a randomized controlled pilot study," Obesity, 2010, 18(8): 1614-1618), herein incorporated by reference in its entirety.

Appendix 2: Schedule of Study Procedures for Example 2

APPENDIX 2

Schedule of Study Procedures for Example 2

|  | Screening Visit 1 (Screen)[1] | Visit 2 (Day 1) (Baseline)[1] | Controlled Treatment Period | | | | | |
|---|---|---|---|---|---|---|---|---|
|  |  |  | Visit 3 (Wk 2)[1] | Visit 4 (Wk 6) | Visit 5 (Wk 10) | Visit 6 (Wk 16)[1] | Visit 7 (Wk 20) | Visit 8 (Wk 26)[1] |
| Informed Consent | X | | | | | | | |
| Eligibility Criteria | X | X | | | | | | |
| Demographics | X | | | | | | | |
| Medical History | X | X | | | | | | |
| Height | X | | | | | | | |
| Electrocardiogram, Physical Exam | X | | | | | | | |
| Chemistry, Hematology, Urinalysis, Drug Screen (urine) | X | | | | | | | |
| Randomization | | X | | | | | | |
| Weight, Vital Signs (BP, HR) | X | X | X | X | X | X | X | X |
| Waist Circumference | | X | | | | X | | X |
| Concomitant Medication Review | X | X | X | X | X | X | X | X |
| Pregnancy Test (urine)[2] | X | X | X | X | X | X | X | X |
| Lipids, Glucose, Insulin[3] | X (glucose, TGs only) | X | | | | X | | X |
| Patient Reported Outcome Measures (BES, ASEX, IWQOL-Lite) | | X | | | | X | | X |
| Query for SAEs | | | X | X | X | X | X | X |
| Minimal Lifestyle Intervention (Usual Care only) | | X | | | | X | | |
| Evaluation to Continue Treatment (NB only) | | | | | | X | | |
| Review CLI participation (NB only) | | X | X | X | X | X | X | X[5] |
| Study Medication Dispensing/Return (NB only) | | X[6] | | X | X | X | X | X[7] |
| Study Medication Compliance (NB only) | | | X | X | X | X | X | X |

The visit window between Visit 1 (Screening) and Visit 2 (Day 1: Baseline) is up to 2 weeks. Visit windows are ±3 days at Visit 3 and 4; ±1 week at Visits 5, 6, 7, and 8 relative to Visit 2.
[1]Subjects should arrive having fasted (no food or beverage except water) overnight for at least 8 hours before this visit. Subjects should receive a call from a member of the study site staff 1 to 3 days prior to these visits (except Visit 1) reminding them to fast for at least 8 hours prior to the visit.
[2]Women of child bearing potential (including peri-menopausal women who have had a menstrual period within one year) only.
[3]Gluocose and triglycerides at Visit 1 are to confirm subject eligibility. Measures at Visit 2 are to obtain baseline values.
[4]Subjects are to be registered for the CLI program and receive instructions at this visit.
[5]Subjects randomized to Usual Care who switch NB and CLI are to be registered for the CLI program and receive instructions at this visit.
[6]Dispensing only at this visit.
[7]Subjects randomized to Usual Care who switch NB and CLI are to be dispensed study medication at the visit.

|  | Uncontrolled Treatment Period | | | | | | | End of Full Participation Visit |
|---|---|---|---|---|---|---|---|---|
|  | Visit 9 (Wk 32) | Visit 10 (Wk 36) | Visit 11 (Wk 42)[1] | Visit 12 (Wk 46) | Visit 13 (Wk 52)[1] | Visit 14 (Wk 65) | Visit 15 (Wk 78)[1] | |
| Weight, Vital Signs (BP, HR) | X | X | X | X | X | X | X | X |
| Waist Circumference | | | X | | X | | X | X |
| Concomitant Medication Review | | | | | X | | X | X |
| Pregnancy Test (urine)[2] | X | X | X | X | X | X | X | X |
| Lipids, Glucosa, Insulin | | | X | | X | | X | |
| Patient Reported Outcome Measures (BES, ASEX, IWQOL-Lite) | | | | | | | | X[3] |

-continued

|  | Uncontrolled Treatment Period | | | | | | | End of Full Participation Visit |
|---|---|---|---|---|---|---|---|---|
|  | Visit 9 (Wk 32) | Visit 10 (Wk 36) | Visit 11 (Wk 42)[1] | Visit 12 (Wk 46) | Visit 13 (Wk 52)[1] | Visit 14 (Wk 65) | Visit 15 (Wk 78)[1] |  |
| Query for SAEs | X | X | X | X | X | X | X | X |
| Evaluation to Continue Treatment (Usual care → NB only) |  |  |  | X |  |  |  |  |
| Review CLI participation | X | X | X | X | X | X | X | X[4] |
| Study Medication Dispensing/Return | X | X | X | X | X | X | X[5] | X[5] |
| Study Medication Compliance | X | X | X | X | X | X | X | X |

Visit windows are ±3 days at Visit 9: ±1 week at Visits 10, 11, 12, and 13 relative to Visit 2; ±2 weeks at Visit 14 and 15 relative to Visit 2.
[1]Subject should arrive having fasted (no food or beverage except water) overnight for at least 8 hours before this visit. Subjects should receive a call from a member of the study site staff 1 to 3 days prior to these visits reminding them to fast for at least 8 hours prior to the visit.
[2]Women of child bearing potential (including peri menopausal women who have had a menstrual period within one year) only.
[3]To be completed if the End of Full Participation Visit occurs during the Controlled Treatment Period.
[4]NB only at this visit.
[5]Returning only at this visit.

TABLE 3

Canadian Cardiovascular Society grading scheme for angina pectoris

| Grade | Description |
|---|---|
| Grade I | Ordinary physical activity does not cause angina, such as walking and climbing stairs. Angina with strenuous or rapid or prolonged exertion at work or recreation. |
| Grade II | Slight limitation of ordinary activity. Walking or climbing stairs rapidly, walking uphill, walking or stair climbing after meals, or in cold, or in wind, or under emotional stress, or only during the few hours after awakening. Walking more than two blocks on the level and climbing more than one flight of ordinary stairs at a normal pace and in normal conditions. |
| Grade III | Marked limitation of ordinary physical activity. Walking one or two blocks on the level and climbing one flight of stairs in normal conditions and at normal pace. |
| Grade IV | Inability to carry on any physical activity without discomfort, angina syndrome may be present at rest. |

Campeau, 1976. Available on the Canadian Cardiovascular Society Website at www.ccs.ca

TABLE 4

New York Heart Association: the stages of heart failure

| Class | Patient symptoms |
|---|---|
| Class I (Mild) | No limitation of physical activity. Ordinary physical activity does not cause undue fatigue, palpitation, or dyspnea (shortness of breath). |
| Class II (Mild) | Slight limitation of physical activity. Comfortable at rest, but ordinary physical activity results in fatigue, palpitation, or dyspnea. |
| Class III (Moderate) | Marked limitation of physical activity. Comfortable at rest, but less than ordinary activity causes fatigue, palpitation, or dyspnea. |
| Class IV (Severe) | Unable to carry out any physical activity without discomfort. Symptoms of cardiac insufficiency at rest. If any physical activity is undertaken, discomfort is increased. |

Available on the Heart Failure Society of America website at www.abouthf.org

What is claimed is:

1. A method of treating a subject at increased risk of a major adverse cardiovascular event for overweight or obesity comprising:
   administering to an overweight or obese subject at increased risk of a major adverse cardiovascular event a therapeutically effective amount of 32 mg sustained release naltrexone per day, or a pharmaceutically acceptable salt thereof, and 360 mg sustained release bupropion per day, or a pharmaceutically acceptable salt thereof;
   wherein said overweight or obese subject is at increased risk of a major adverse cardiovascular event if said subject has been diagnosed as having cardiovascular disease with at least one risk factor selected from the group consisting of:
      a history of documented myocardial infarction ≥3 months prior to said identification;
      a history of coronary revascularization including coronary artery bypass graft surgery, stent placement, percutaneous transluminal coronary angioplasty, or laser atherectomy;
      angina with ischemic changes, ECG changes on a graded exercise test, or positive cardiac imaging study;
      ankle brachial index <0.9 assessed by simple palpation within prior 2 years of said identification; and
      ≥50% stenosis of a coronary, carotid, or lower extremity artery within prior 2 years of said identification, and
   wherein said subject is treated for at least 16 weeks.

2. The method of claim 1, wherein said subject does not have Type 2 diabetes mellitus with at least 2 risk factors selected from the group consisting of:
   hypertension controlled with or without pharmacotherapy at ≤145/95 mm Hg; dyslipidemia requiring pharmacotherapy;
   documented low HDL cholesterol, ≤50 mg/dL in women or ≤40 mg/dL in men, within prior 12 months of said identification; and
   current tobacco smoker.

3. The method of claim 1, further comprising providing said subject with a web-based weight management program, a phone-based weight management program, or a combination thereof.

4. The method of claim 3, wherein said phone-based weight management program comprise one or more coaching calls to said subject.

5. The method of claim 3, wherein said phone-based weight management program optionally comprises one or more web coaching tools.

6. The method of claim 3, wherein said web-based or phonebased weight management program provides said subject with one or more of behavioral, nutritional or fitness education.

7. The method of claim 3, wherein said weight management program comprises one or more activities selected from the group of weekly recording of said subject's weight, daily recording of said subject's food intake, and daily recording of said subject's activity.

8. The method of claim 3, wherein said weight management program comprises said subject recording said subject's food intake, wherein said program can track calories for said recorded food intake using a computer database of calories for specific food and/or meals.

9. The method of claim 8, wherein the subject achieves a percentage of weight loss of at least 5%.

10. The method of claim 1, wherein the subject does not receive an intensive behavioral modification (BMOD) program for weight loss.

11. The method of claim 1, wherein said treatment with naltrexone and bupropion does not increase said subject's risk of a major adverse cardiovascular event.

12. The method of claim 1, wherein said treatment with naltrexone and bupropion decreases said subject's risk of a major adverse cardiovascular event.

13. The method of claim 12, wherein said sustained release naltrexone, or a pharmaceutically acceptable salt thereof is administered in two 8 mg doses twice daily, and said sustained release bupropion, or a pharmaceutically acceptable salt thereof is administered in two 90 mg doses twice daily.

14. The method of claim 1, wherein said major adverse cardiovascular event is cardiovascular death, nonfatal myocardial infarction, or nonfatal stroke.

15. A method of treating a subject at increased risk of a major adverse cardiovascular event for overweight or obesity comprising:
administering to an overweight or obese subject at increased risk of a major adverse cardiovascular event a therapeutically effective amount of 32 mg sustained release naltrexone per day, or a pharmaceutically acceptable salt thereof, and 360 mg sustained release bupropion per day, or a pharmaceutically acceptable salt thereof;
wherein said overweight or obese subject is at increased risk of a major adverse cardiovascular event if said subject has been diagnosed as having cardiovascular disease with at least one risk factor selected from the group consisting of:
a history of documented myocardial infarction >3 months prior to said identification;
a history of coronary revascularization including coronary artery bypass graft surgery, stent placement, percutaneous transluminal coronary angioplasty, or laser atherectomy;
angina with ischemic changes, ECG changes on a graded exercise test, or positive cardiac imaging study;
ankle brachial index <0.9 assessed by simple palpation within prior 2 years of said identification; and
>50% stenosis of a coronary, carotid, or lower extremity artery within prior 2 years of said identification; and
wherein the subject is administered said sustained release naltrexone, or a pharmaceutically acceptable salt thereof, and said sustained release bupropion, or a pharmaceutically acceptable salt thereof, in a tablet containing 8 mg of sustained release naltrexone and 90 mg of sustained release bupropion.

16. The method of claim 15, wherein said sustained release naltrexone, or a pharmaceutically acceptable salt thereof is administered in two 8 mg doses twice daily, and said sustained release bupropion, or a pharmaceutically acceptable salt thereof is administered in two 90 mg doses twice daily.

17. A method of treating a subject at increased risk of a major adverse cardiovascular event for overweight or obesity comprising:
administering to an overweight or obese subject at increased risk of a major adverse cardiovascular event a therapeutically effective amount of 32 mg sustained release naltrexone per day, or a pharmaceutically acceptable salt thereof, and 360 mg sustained release bupropion per day, or a pharmaceutically acceptable salt thereof;
wherein said overweight or obese subject is at increased risk of a major adverse cardiovascular event if said subject has been diagnosed as having cardiovascular disease with at least one risk factor selected from the group consisting of:
a history of documented myocardial infarction >3 months prior to said identification;
a history of coronary revascularization including coronary artery bypass graft surgery, stent placement, percutaneous transluminal coronary angioplasty, or laser atherectomy;
angina with ischemic changes, ECG changes on a graded exercise test, or positive cardiac imaging study;
ankle brachial index <0.9 assessed by simple palpation within prior 2 years of said identification; and
>50% stenosis of a coronary, carotid, or lower extremity artery within prior 2 years of said identification; and
wherein said major adverse cardiovascular event is cardiovascular death, nonfatal myocardial infarction, or nonfatal stroke.

18. The method of claim 17, wherein said major adverse cardiovascular event is cardiovascular death.

19. The method of claim 18, wherein said sustained release naltrexone, or a pharmaceutically acceptable salt thereof is administered in two 8 mg doses twice daily, and said sustained release bupropion, or a pharmaceutically acceptable salt thereof is administered in two 90 mg doses twice daily.

20. The method of claim 19, wherein the subject is administered said sustained release naltrexone, or a pharmaceutically acceptable salt thereof, and said sustained release bupropion, or a pharmaceutically acceptable salt thereof, in a tablet containing 8 mg of sustained release naltrexone and 90 mg of sustained release bupropion.

* * * * *